(12) United States Patent
Cooks et al.

(10) Patent No.: US 9,733,228 B2
(45) Date of Patent: Aug. 15, 2017

(54) METHODS OF ANALYZING CRUDE OIL

(71) Applicant: Purdue Research Foundation, West Lafayette, IN (US)

(72) Inventors: Robert Graham Cooks, West Lafayette, IN (US); Fred Paul Mark Jjunju, West Lafayette, IN (US); Anyin Li, West Lafayette, IN (US); Iman S. Rogan, Thuwal (SA)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/426,879

(22) PCT Filed: Jan. 23, 2014

(86) PCT No.: PCT/US2014/012746
§ 371 (c)(1),
(2) Date: Mar. 9, 2015

(87) PCT Pub. No.: WO2014/120552
PCT Pub. Date: Aug. 7, 2014

(65) Prior Publication Data
US 2015/0309001 A1    Oct. 29, 2015

Related U.S. Application Data

(60) Provisional application No. 61/759,097, filed on Jan. 31, 2013.

(51) Int. Cl.
*H01J 49/10* (2006.01)
*G01N 33/28* (2006.01)
(Continued)

(52) U.S. Cl.
CPC ....... *G01N 33/2823* (2013.01); *G01N 30/724* (2013.01); *G01N 30/7266* (2013.01);
(Continued)

(58) Field of Classification Search
None
See application file for complete search history.

(56) References Cited

U.S. PATENT DOCUMENTS 3,000,836 A    9/1961  Ginsburg
3,334,233 A    8/1967  Veal
(Continued)

FOREIGN PATENT DOCUMENTS

CN    101820979 A    9/2010
CN    102414778 A    4/2012
(Continued)

OTHER PUBLICATIONS

Jjunji et al., "in situ analysis of corrosion inhibitors using a portable mass spectrometer with paper spray ionization", Analyst, 138,3740, first published on-line May 9, 2013.*
(Continued)

*Primary Examiner* — Michael Logie
(74) *Attorney, Agent, or Firm* — Brown Rudnick LLP; Adam M. Schoen

(57) ABSTRACT

The invention generally relates to methods of analyzing crude oil. In certain embodiments, methods of the invention involve obtaining a crude oil sample, and subjecting the crude oil sample to mass spectrometry analysis. In certain embodiments, the method is performed without any sample pre-purification steps.

7 Claims, 20 Drawing Sheets

(51) Int. Cl.
*G01N 30/72* (2006.01)
*H01J 49/16* (2006.01)
*H01J 49/04* (2006.01)
*H01J 49/00* (2006.01)

(52) U.S. Cl.
CPC .......... *H01J 49/0031* (2013.01); *H01J 49/04* (2013.01); *H01J 49/10* (2013.01); *H01J 49/164* (2013.01)

(56) References Cited

U.S. PATENT DOCUMENTS

| | | | |
|---|---|---|---|
| 4,755,670 A | 7/1988 | Syka et al. | |
| 4,757,198 A | 7/1988 | Korte et al. | |
| 4,828,547 A | 5/1989 | Sahi et al. | |
| 4,885,076 A | 12/1989 | Smith et al. | |
| 5,141,868 A | 8/1992 | Shanks et al. | |
| 5,152,177 A | 10/1992 | Buck et al. | |
| 5,288,646 A | 2/1994 | Lundsgaard et al. | |
| 5,583,281 A | 12/1996 | Yu | |
| 6,297,499 B1 | 10/2001 | Fenn | |
| 6,452,168 B1 | 9/2002 | McLuckey et al. | |
| 6,477,238 B1 | 11/2002 | Schneider et al. | |
| 6,627,881 B1 | 9/2003 | Bertrand et al. | |
| 6,982,416 B2 | 1/2006 | Villinger et al. | |
| 6,992,284 B2 | 1/2006 | Schultz et al. | |
| 7,005,635 B2 | 2/2006 | Ahern et al. | |
| 7,010,096 B1 | 3/2006 | Wooding | |
| 7,154,088 B1 | 12/2006 | Blain et al. | |
| 7,171,193 B2 | 1/2007 | Hoffman | |
| 7,223,969 B2 | 5/2007 | Schultz et al. | |
| 7,259,019 B2 | 8/2007 | Pawliszyn et al. | |
| 7,384,793 B2 | 6/2008 | McCash et al. | |
| 7,384,794 B2 | 6/2008 | Pawliszyn | |
| 7,510,880 B2 | 3/2009 | Gross et al. | |
| 7,544,933 B2 | 6/2009 | Cooks et al. | |
| 7,564,027 B2 | 7/2009 | Finch et al. | |
| 7,714,281 B2 | 5/2010 | Musselman | |
| 7,915,579 B2 | 3/2011 | Chen et al. | |
| 7,930,924 B2 | 4/2011 | Krogh et al. | |
| 8,030,088 B2 | 10/2011 | McCash et al. | |
| 8,076,639 B2 | 12/2011 | Cooks et al. | |
| 8,294,892 B2 | 10/2012 | Sardashti et al. | |
| 8,330,119 B2 | 12/2012 | Chen et al. | |
| 8,334,505 B2 | 12/2012 | Robinson et al. | |
| 8,421,005 B2 | 4/2013 | Musselman | |
| 8,481,922 B2 | 7/2013 | Musselman | |
| 8,704,167 B2 | 4/2014 | Cooks et al. | |
| 8,710,437 B2 | 4/2014 | Cooks et al. | |
| 8,816,275 B2 | 8/2014 | Ouyang et al. | |
| 8,859,956 B2 | 10/2014 | Ouyang et al. | |
| 8,859,958 B2 | 10/2014 | Ouyang et al. | |
| 8,859,959 B2 | 10/2014 | Ouyang et al. | |
| 8,859,986 B2 | 10/2014 | Cooks et al. | |
| 8,895,918 B2 | 11/2014 | Cooks et al. | |
| 8,932,875 B2* | 1/2015 | Cooks | H01J 49/0431 250/282 |
| 9,165,752 B2* | 10/2015 | Cooks | H01J 49/0431 |
| 2002/0034827 A1 | 3/2002 | Singh et al. | |
| 2002/0055184 A1 | 5/2002 | Naylor et al. | |
| 2002/0123153 A1 | 9/2002 | Moon et al. | |
| 2003/0141392 A1 | 7/2003 | Nilsson et al. | |
| 2003/0180824 A1 | 9/2003 | Mpock et al. | |
| 2003/0199102 A1 | 10/2003 | Ostrup | |
| 2004/0011954 A1 | 1/2004 | Park | |
| 2004/0075050 A1 | 4/2004 | Rossier et al. | |
| 2004/0245457 A1 | 12/2004 | Granger et al. | |
| 2005/0112635 A1 | 5/2005 | Gentle et al. | |
| 2005/0117864 A1 | 6/2005 | Dziekan et al. | |
| 2005/0247870 A9 | 11/2005 | Park | |
| 2006/0093528 A1 | 5/2006 | Banerjee et al. | |
| 2006/0118713 A1 | 6/2006 | Matsui et al. | |
| 2006/0192107 A1 | 8/2006 | DeVoe et al. | |
| 2006/0200316 A1 | 9/2006 | Kanani et al. | |
| 2006/0249668 A1 | 11/2006 | Goldberg et al. | |
| 2007/0003965 A1 | 1/2007 | Ramsay et al. | |
| 2007/0025881 A1 | 2/2007 | Thompson et al. | |
| 2007/0151232 A1 | 7/2007 | Dalla Betta et al. | |
| 2007/0187589 A1 | 8/2007 | Cooks et al. | |
| 2008/0083873 A1 | 4/2008 | Giardina | |
| 2008/0128608 A1 | 6/2008 | Northen et al. | |
| 2008/0179511 A1 | 7/2008 | Chen et al. | |
| 2008/0210856 A1* | 9/2008 | Eide | G01N 30/724 250/282 |
| 2008/0272294 A1 | 11/2008 | Kovtoun | |
| 2008/0283742 A1 | 11/2008 | Takeuchi et al. | |
| 2009/0071834 A1 | 3/2009 | Hafeman et al. | |
| 2009/0090856 A1 | 4/2009 | Grant et al. | |
| 2009/0127454 A1 | 5/2009 | Ritchie et al. | |
| 2009/0152371 A1 | 6/2009 | Stark et al. | |
| 2009/0280300 A1 | 11/2009 | Craighead et al. | |
| 2009/0306230 A1 | 12/2009 | Semikhodskii et al. | |
| 2009/0309020 A1 | 12/2009 | Cooks et al. | |
| 2010/0001181 A1 | 1/2010 | Moini | |
| 2010/0019143 A1 | 1/2010 | Dobson et al. | |
| 2010/0059689 A1 | 3/2010 | Horiike et al. | |
| 2010/0230587 A1 | 9/2010 | Marshall et al. | |
| 2010/0301209 A1 | 12/2010 | Ouyang et al. | |
| 2011/0108724 A1 | 5/2011 | Ewing et al. | |
| 2011/0108726 A1 | 5/2011 | Hiraoka et al. | |
| 2011/0133077 A1 | 6/2011 | Henion et al. | |
| 2011/0193027 A1 | 8/2011 | Mackenzie et al. | |
| 2011/0210265 A1 | 9/2011 | Lozano et al. | |
| 2012/0018629 A1 | 1/2012 | Eikel et al. | |
| 2012/0119079 A1* | 5/2012 | Ouyang | H01J 49/0431 250/282 |
| 2012/0153139 A1 | 6/2012 | Qian et al. | |
| 2013/0023005 A1 | 1/2013 | Chen et al. | |
| 2013/0112866 A1 | 5/2013 | Ouyang et al. | |
| 2013/0112867 A1 | 5/2013 | Ouyang et al. | |
| 2013/0273560 A1 | 10/2013 | Cooks et al. | |
| 2013/0299694 A1 | 11/2013 | Sato et al. | |
| 2014/0165701 A1* | 6/2014 | Wu | G01N 27/62 73/23.38 |

FOREIGN PATENT DOCUMENTS

| | | | | |
|---|---|---|---|---|
| JP | 2011007690 A | | 1/2011 | |
| WO | 0153819 A1 | | 7/2001 | |
| WO | 03104814 A2 | | 12/2003 | |
| WO | WO 2009023361 A2 * | | 2/2009 | H01J 49/0495 |
| WO | WO 2010127059 A1 * | | 11/2010 | H01J 49/0431 |
| WO | WO 2012094227 A2 * | | 7/2012 | H01J 49/0341 |
| WO | 2012170301 A1 | | 12/2012 | |

OTHER PUBLICATIONS

Lui et al. "Development, characterization and application of paper spray ionization", Anal. Chem. 2010.*

Eckert et al., "chemical characterization of crude petroleum using nanospray desorption electrospray ionization coupled with high-resolution mass spectrometry", Analytical Chemistry, 2011.*

Gough et al. "Analysis of Oilfield Chemicals by Electrospray Mass Spectrometry", Rapid Communications in Mass spectrometry, 1999.*

Oradu et al. "multistep mass spectrometry methodology for direct characterization of polar lipids in green microalgae using paperspray ionization", Anal. Chem., 2012.*

Wang et al., "Paper Spray for Direct Analysis of Complex Mixtures Using Mass Spectrometry", Angew. Chem. Int. Ed. 2010.*

Douglas et al. "Paper Spray Ionisation for the analysis of Naphthenic Acids", Irving k. Barber School of the Arts and Sciences, 7th Annual Undergraduate Research Conference, pp. 5-6, 2012.*

Atlas, et al., "Oil biodegradation and bioremediation: a tale of the two worst spilss in U.S. history" Environmental Science & Technology, 2011,45,6709-6715.

Cody et al., 2005, Versatile New Ion Source for the Analysis of Materials in Open Air under Ambient Condition, Anal. Chem. 77:2297-2302.

(56) References Cited

OTHER PUBLICATIONS

Cooks et al., (2011), New ionization methods and miniature mass spectrometers for biomedicine: DESI imaging for cancer diagnostics and paper spray ionization for therapeutic drug monitoring, Faraday Discussions 149:247-267, published in United Kingdom.
Cooks et al., 2006, Ambient Mass Spectrometry, Science 311:1566-1570.
Extended European Search Report Mailed Oct. 18, 2016 for European Patent Application No. 14818223.1 (5 Pages).
Extended European Search Report mailed Sep. 7, 2016 for European Patent Application No. 14745610.7 (11 Pages).
Ferguson et al., Direct Ionization of Large Proteins and Protein Complexes by Desorption Electrospray Ionization-Mass Spectrometry, Anal. Chem. 2011, 83, 6468-6473.
Gao, L.; Sugiarto, A.; Harper, J. D.; Cooks, R. G.; Ouyang, Z. Anal. Chem., 2008, 80, 7198-7205.
Gaskell, 1997, Electrospray: Principles and Practice, J. Mass. Spect., 32:677-688.
Gough et al., "Molecular Monitoring of Residual Corrosion Inhibitor Actives in Oilfields Fluids: Implications for Inhibitor Performance" Corrosion, 98 Paper No. 33 (1998) (12 Pages).
Harris et al., 2011, Ambient Sampling/Ionization Mass Spectrometry: Applications and Current Trends Anal. Chem., 83:4508-4538.
Huang et al., 2010, Ambient Ionization Mass Spectrometry, Ann. Rev. Anal. Chem., 3:43-65.
Ifa et al., Desorption electrospray ionization and other ambient ionization methods: current progress and preview, Analyst 135, 669-681 (2010), published in United Kingdom.
International Preliminary Report of Patentability for PCT/US2010/032881 from International Bureau, mailed Nov. 10, 2011, (10 pages).
International Preliminary Report on Patentability for PCT/US2009/045649 mailed Dec. 9, 2010, (7 pages).
International Search Report and Written Opinion for PCT/US2010/032881 for International Searching Authority, mailed Aug. 4, 2010, (10 pages).
International Search Report and Written Opinion mailed on Aug. 27, 2014, for International Patent Application No. PCT/US14/34767, filed Apr. 21, 2014, (20 pages).
International Search Report and Written Opinion of the International Searching Authority Mailed Jul. 8, 2014 for International Application No. PCT/US2014/012746 (27 Pages).
International Search Report issued in PCT/US2014/011000 on Apr. 19, 2014.
Joyce, Special Report: Glassware, Plasticware Compete in Labs, May 27, 1991, The Scientist Magazine.
Kujawinski et al., "Fate of Dispersants Associated with the Deepwater Horizon Oil Spill" Science and Technology, 2011, 45, 1298-1306.
Liu et al., Recent advances of electrochemical mass spectrometry, Analyst, 2013, 138, 5519-5539.
Liu et al., Signal and charge enhancement for protein analysis by liquid chromatography-mass spectrometry with desorption electrospray ionization, International Journal of Mass Spectrometry 325-327 (2012) 161-166.
Lozano, et al. "Ionic Liquid Ion Sources: Characterization of Externally Wetted Emitters", Journal of Colloid and Interface Science 282 (2005) 415-421.
Lui et al., Measuring Protein?Ligand Interactions Using Liquid Sample Desorption Electrospray Ionization Mass Spectrometry, Anal. Chem. 2013, 85, 11966?11972.
Martin A. Claydon et al. "The Rapid Identification of Intact Microorganisms Using Mass Spectrometry", Nature Biotechnology, vol. 14, No. 11, Nov. 1, 1996, pp. 1584-1586 (3 Pages).
Miao et.al., Direct Analysis of Liquid Samples by Desorption Electrospray Ionization-Mass Spectrometry (DESI-MS), J Am Soc Mass Spectrom 2009, 20, 10-19.
Nemes, P., Ambient mass spectrometry for in vivo local analysis and in situ molecular tissue imaging, TrAC-Trends in Analytical Chemistry 34, 22-33 (2012), published in United Kingdom.
Notification Concerning Transmittal of International Preliminary Report on Patentability for International Application No. PCT/US2014/034767 Dated Jan. 7, 2016 (7 Pages).
Ratcliffe et al., 2007, Surface Analysis under Ambient Conditions Using Plasma-Assisted Desorption/Ionization Mass Spectrometry, Anal. Chem., 79:6094-6101.
Ren, Yue et al., "Direct Mass Spectrometry Analysis of Untreated Samples Ultralow Amounts Using Extraction Nano-Electrospray", Analytical Methods, vol. 5, No. 23, Sep. 20, 2013, pp. 6686-6692 (7 Pages).
Sokol, E.; Noll, R. J.; Cooks, R. G.; Beegle, L. W.; Kim, H. I.; Kanik, I.; Int. J. Mass Spectrom., 2011, In Press, Corrected Proof.
Soparawalla et al., Analyst, 2011, 136, 4392-4396.
Takats et al., Mass spectrometry sampling under ambient conditions with desorption electrospray ionization, Science 306, 471-473 (2004), published in USA.
Thibodeaux et al., "Marine Oil Fate: Knowledge Gaps, Basic Research, and Development Needs; a Perspective based on the Depwater Horizon Spill" Environmental Engineering Science, 2011, 28, 87-93.
Valentine, et al., "Propane respiration jump-starts microbial response to deep oiil spill", Science, 2010, 330(208-211).
Yuan Su et al., "Quantitative Paper Spray Mass Spectrometry Analysis of Drugs of Abuse", The Analyst, vol. 138, No. 16, Jan. 1, 2013, p. 4443 (5 Pages).
Zhang et al., Electrochemistry-Assisted Top-Down Characterization of Disulfide-Containing Proteins, Anal Chem. Apr. 17, 2012; 84(8): 1-7.
Zhang et al., Mass Spectrometric Analysis of Thiol Proteins/Peptides Following Selenamide Derivatization and Electrolytic Reduction of Disulfide Bonds, Dec. 2012, pp. 240.
Zhang et al., Paper Spray Ionization of Noncovalent Protein Complexes, Jan. 1, 2014, Anal. Chem. A-E.

* cited by examiner

METHODS OF ANALYZING CRUDE OIL

RELATED APPLICATION

The present application claims the benefit of and priority to U.S. provisional patent application Ser. No. 61/759,097, filed Jan. 31, 2013, the content of which is incorporated by reference herein in its entirety.

GOVERNMENT SUPPORT

This invention was made with government support under DE-FG02-06ER15807 awarded by Department of Energy. The government has certain rights in the invention.

FIELD OF THE INVENTION

The invention generally relates to methods of analyzing crude oil.

BACKGROUND

Pipelines are generally the most economical way to transport large quantities of crude oil, refined oil products or natural gas over land. Steel pipes are commonly used, which can be subject to both internal and external corrosion. Corrosion protection is a critical process to ensure continuous pipeline operation.

Corrosion of oil transmission pipelines can result in leakage and large scale oil spills that are destructive of the ecosystem and pollute drinking water supplies (Sastri, Corrosion Inhibitors: Principles and applications, J. Wiley & Sons, New York, 2001, Ch 1, pp 5-30; Sacher, et al., J. Chromatogr, A, 1997, 764, 85-93; Zhao et al. Materials and Corrosion, 2004, 55, 684-688; Son, NACE International Corrosion Conference Series, 2007, 07618; Valentine, et al., Science, 2010, 330 208-211; Kujawinski, et al., Science & Technology, 2011, 45, 1298-1306; Thibodeaux, et al., Environmental Engineering Science, 2011, 28, 87-93; Bjorndal, et al., Science, 2011, 331, 537-538; and Atlas et al., Environmental Science & Technology, 2011, 45, 6709-6715). Corrosion is typically inhibited through addition to crude petroleum of oil-soluble heterocyclic compounds, such as quaternary ammonium salts and ionic liquids (Quraishi et al., Am. Oil Chem. Soc., 2000, 77, 1107-1111, Treybig et al., U.S. Pat. No. 4,957,640; Derek et al., U.S. Pat. No. 4,235,838; and Young et al., U.S. Pat. No. 6,645,399). Successful inhibition depends on the amount of inhibitor, and so measurement of inhibitor levels in crude oil is of great interest, especially in long-distance transfer pipelines (Nyborg et al., NACE-International, Corrosion Conference Series, 2012, 6, 4582-4590; KvarekvUl, NACE-International Corrosion, Conference Series, 2012, 6, 4329-4352; and Dugstad et al., NACE-International, Corrosion Conference Series, 2012, 5, 3573-3586).

Currently, no standard method exists for direct in-field monitoring of residual levels of corrosion inhibitors. Gas chromatography or high performance liquid chromatography combined with mass spectrometry (GC-MS or HPLC-MS) is the most widely adopted method for ex-situ quantification of residual corrosion inhibitors and other oil constituents. (Sacher et al., J. Chromatogr, A, 1997, 764, 85-93; Son, NACE International Corrosion Conference Series, 2007, 07618; Huhn et al., J. Anal. Chem., 1995, 351, 563-566; Gough et al., NACE-International, Corrosion, 98 paper, No 33; Schwartz et al., Anal. Chem., 1990, 62, 1809-1818; Chiang et al., Chemistry of Materials, 1992, 4, 245-247; Hsu, Anal. Chem., 1993, 65, 767-771; March, J. Mass Spectrom., 1997, 32, 351-369; and He et al., Energy Fuels., 2011, 25, 4770-4775). Although highly sensitive and specific, these methods are time consuming, requiring numerous sample purification and preparation steps prior to analysis. Due to the sample work-up required prior to analysis, samples need to be taken to the laboratory for analysis.

SUMMARY

The invention provides methods for analyzing a crude oil sample by mass spectrometry in an unmodified form from which it was obtained. Accordingly, methods of the invention may be performed without any sample pre-purification steps. Aspects of the invention are accomplished using wetted porous material as a substrate for the mass spectrometry analysis. An unmodified crude oil sample, such as that extracted from an oil transmission pipeline, is directly introduced to a porous substrate. Solvent and voltage is applied to the substrate to generate ions of an analyte in the sample. Those ions are directed into and analyzed by a mass spectrometer. In that manner, methods of the invention provide rapid and efficient in-field mass spectrometry techniques for the analysis of crude oil, such as monitoring corrosion inhibitors in the crude oil in transmission pipelines.

In certain aspects, the invention provides methods for analyzing a crude oil sample that involve obtaining a crude oil sample, and subjecting the crude oil sample to mass spectrometry analysis. The methods of the invention may be performed without any sample pre-purification steps, i.e., the sample is taken directly from its source and is directly analyzed by mass spectrometry without any additional modification to the sample. In certain embodiments, the mass spectrometry analysis is performed in an ambient environment.

In certain embodiments, the mass spectrometry analysis involves introducing the crude oil sample to a porous substrate, applying solvent (e.g., a mixture of methanol and acetonitrile) and voltage to the substrate to generate ions of an analyte in the crude oil sample, and analyzing the ions using a mass spectrometer. Numerous different types of porous substrates may be used with methods of the invention, and such substrates are described in greater detail below. An exemplary porous substrate is paper, such as filter paper. The mass spectrometer may be a bench-top mass spectrometer or a miniature mass spectrometer. In certain embodiments, the mass spectrometer or miniature mass spectrometer is coupled to a discontinuous atmospheric pressure interface.

Methods of the invention may be used to analyze numerous different types of analytes in crude oil. In certain embodiments, the analyte in the crude oil is a corrosion inhibitor. The corrosion inhibitor may include at least one alkyl ammonium salt, such as tetradodecylammonium bromide, benzylhexadecyldimethylammonium chloride, or a combination thereof.

Other aspects of the invention provide methods for quantifying a corrosion inhibitor in crude oil. The methods involve obtaining a crude oil sample including a corrosion inhibitor, subjecting the crude oil sample to mass spectrometry analysis, and quantifying the corrosion inhibitor in the crude oil sample based on results of the mass spectrometry analysis, in which the method is performed without any sample pre-purification steps.

BRIEF DESCRIPTION OF THE DRAWINGS

FIG. 3A shows tetraoctyl ammonium bromide at m/z 466.6. FIG. 3B shows tetrabutylammonium hexafluorophosphate at m/z 242. Insert (i) shows the isotopic distribution of the analyte ion and inserts (ii)-(vi) show MS/MS CID data for selected ions, again using 100 pg of analyte in 1 µL of oil.

FIG. 5A is tetraoctyl ammonium bromide, FIG. 5B is benzylhexadecyldimethyl ammonium chloride in vacuum pump oil artificial mixture, and FIGS. 5C-D are the CID mass spectra of the samples respectively.

DETAILED DESCRIPTION

Figure 1:
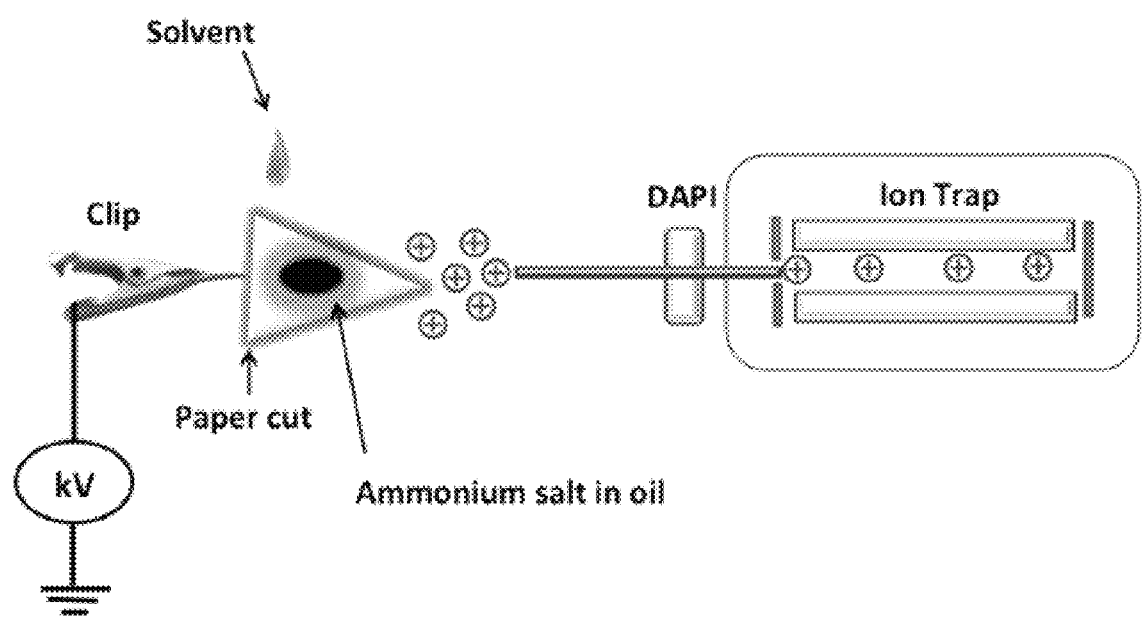
FIG. 1 is a schematic showing paper spray mass spectrometry for in-situ analysis of corrosion inhibitors in oil using a miniature mass spectrometer.

The invention generally relates to methods for analyzing crude oil. Crude oil refers to a naturally occurring, unrefined petroleum product composed of hydrocarbon deposits. Crude oil is refined to produce petroleum products such as gasoline, diesel and various forms of petrochemicals. Methods of the invention can analyze any analyte within the crude oil. An analyte refers to any substance or chemical in the crude oil that can be identified and/or measured. The analyte may be a naturally occurring substance or chemical in the crude oil (e.g., paraffinsm naphthenes, aromatics, or asphaltics). Alternatively, the analyte may be a non-naturally occurring substance or chemical that is found in the crude oil. Exemplary non-naturally occurring substances or chemicals that are found in crude oil include corrosion inhibitors, emulsion breakers, hydrogen sulfide controllers, paraffin control additives, scale inhibitors, hydrate inhibitors (e.g., ethylene glycol and methanol), dehydrators (e.g., triethylene glycol), bactericides (e.g., quaternary amine salt, amine acetate, and gluteraldehyde), and defoamers (e.g., silicones and polyglycol esters).

A corrosion inhibitor refers to a chemical compound that, when added to a liquid or gas, decreases the corrosion rate of a material, typically a metal or an alloy. Corrosion inhibitors are further described, for example in Son ("Developments In The Laboratory Evaluation Of Corrosion Inhibitors: A Review", NACE Corrosion 2007 Conference and Expo, Paper number 07618); Son (Corrosion, 2004, NACE International Conference, paper number 04373); Buck et al. (U.S. Pat. No. 5,152,177); Quraishi et al. (Am. Oil Chem. Soc., 2000, 77, 1107-1111); Treybig et al. (U.S. Pat. No. 4,957,640); Derek et al. (U.S. Pat. No. 4,235,838); and Young et al. (U.S. Pat. No. 6,645,399), the content of each of which is incorporated by reference herein in its entirety. In certain embodiments, the corrosion inhibitor includes alkyl ammonium salts, such as tetradodecylammonium bromide and/or benzylhexadecyldimethylammonium chloride. Commercially available corrosion inhibitors are sold by Weatherford, such as those described in Table 1 below.

TABLE 1

Alpha 1018 - 75 to 80% active alkyl pyridine benzyl quaternary ammonium
chloride used to formulate corrosion preventives for applications in oil well
drilling, completion, production, and water flood systems. Highly cationic amine compound that is normally diluted or formulated with other additives,
such as nonionic surfactants and alcohols, for application purposes.
Alpha 1505 - 48 to 52% active benzyl quaternary ammonium chloride used to
formulate corrosion preventives for applications in oil well drilling, completion, production, and water flood systems. Highly cationic amine compound that is normally diluted or formulated with other additives for application purposes.
Alpha 3013 - 85 to 90% active blend of alkyl benzyl quaternary ammonium
chloride, aliphatic amines, and anionic surfactant to formulate corrosion inhibitors for use in oil and gas pipelines, producing wells, and water flooding
systems. Also provides corrosion protection for oil well acidizing, high temperature gas wells, and refinery applications. Highly cationic amine compound that is normally diluted (25% by volume with water) or formulated
with other additives for application purposes.
Alpha 3058 - 40% active blend of alkyl pyridine benzyl quaternary ammonium chloride, nonionic surfactant, and acetylenic alcohols to formulate
corrosion inhibitors for use in oil and gas pipelines, producing wells, and water flood systems. Effective corrosion inhibitor for oil well acidizing additives, high temperature gas wells, or refinery applications. Highly cationic amine compound that is normally diluted or formulated with other additives for application purposes.
Alpha 3149 - Blend of alkyl pyridine benzyl quaternary ammonium chloride,
nonionic and anionic surfactants to formulate corrosion inhibitors for use in
oil and gas producing wells, gathering systems, and water flooding systems.
Effective in high temperature gas wells and refinery applications. Can be diluted with alcohols, glycols, or water-alcohol solutions for application purposes.
Alpha 3412 - 75 to 80% active blend of alkyl pyridine benzyl quaternary ammonium chloride, nonionic and anionic surfactants used to formulate TABLE 1-continued corrosion inhibitors for use in oil and gas producing wells, gathering systems,
and water flooding systems. Can be diluted with alcohols, glycols, or water-
alcohol solutions for application purposes.
Alpha 3435 - 53 to 57% active blend of alkyl pyridine benzyl quaternary ammonium chloride salt and nonionic surfactant designed as a corrosion inhibitor for use in oil well drilling, completion, production, and water flooding systems. Cationic amine compound that can be used as a surfactant
for well clean out and stimulation operations.
Alpha 3444 - 77 to 83% active blend of alkyl pyridine benzyl quaternary ammonium chloride, nonionic and anionic surfactants used to formulate corrosion inhibitors for use in oil and gas producing wells, gathering systems,
and water flooding systems. Highly cationic amine compound that can be diluted with alcohols, glycols, or water/alcohol blends.
Alpha 7368 - 23 to 28% active amine, quaternary ammonium chloride, and
sulfite blend used as corrosion preventives in oil well drilling completion, producing, and water flooding systems. Recommended for use in saltwater packer fluid and drilling fluids. Concentration range of 500 to 2000 ppm when used as a hydrostatic corrosion inhibitor.
Alpha 7369 - 23 to 28% active amine, quaternary ammonium chloride, and
sulfite blend used as corrosion preventives in oil well drilling completion, producing, and water flooding systems. Recommended for use in saltwater packer fluid and drilling fluids. Concentration range of 500 to 2000 ppm when used as a hydrostatic corrosion inhibitor.
Alpha 2095 - 68 to 72% active cocoamine diquaternary ammonium chloride
used to formulate corrosion preventives for applications in oil well drilling,
completion, production, and water flood systems. Highly cationic amine compound that is normally diluted (50% by weight with water) or formulated
with other additives for application purposes.
Alpha 2129 - 83 to 87% active cocomine quaternary ammonium chloride in
an aqueous solution that is used as a surfactant to improve water injectivity in
water floods. Can be used as a corrosion preventative in water floods or in produced water handling systems.
CE-152 - 78 to 82% active alkyl dimethyl benzyl quaternary ammonium chloride used as a corrosion preventative for water systems or downhole producing oil wells. The alkyl groups are C-12, C-14, and C-16. Effective against sulfide corrosion. Often blended with demulsifiers to "wet" sulfides and other solids that cause emulsion problems.
Alpha 1153 (CE-123)/(CI-811) - 98 to 100% active imidazoline derived from
monobasic fatty acids to formulate corrosion inhibitors for use in drilling, production, transporting, and refining of crude oil. Can be formulated with inorganic and organic acids to form liquid, water-soluble salts for use as corrosion preventives, emulsifiers, wetting agents, or scale preventives. Used
in concentrated form or diluted for application purposes.
Alpha 1215 - 98 to 100% active polyamide derived from fatty acids used to
formulate thermally stable corrosion preventives for applications in drilling,
production, transporting, and refining of crude oil. Can be formulated with inorganic and organic acids to form water-soluble salts for use as corrosion
preventives, emulsifiers, wetting agents, or scale preventives. Highly cationic
amine that can be used in concentrated form or diluted for application purposes.
Alpha 1378 - 78 to 82% active modified amido polyamine derived from oleyl
fatty acids to formulate corrosion inhibitors for use in drilling, production, transporting, and refining of crude oil. Can be formulated with inorganic and
organic acids to form liquid, water-soluble salts for use as corrosion preventives, emulsifiers, wetting agents, or scale preventives.
Alpha 1386 - 98 to 100% active alkylamidomine derived from monobasic acids to formulate corrosion inhibitors for use in drilling, production, transporting, and refining of crude oil. Can be formulated with inorganic and
organic acids to form liquid, water-soluble salts for use as corrosion preventives, emulsifiers, wetting agents, or scale preventives.
Alpha 3198 - 98 to 100% active complex polyamine derived from fatty acids

TABLE 1-continued used to formulate thermally stable corrosion preventives for applications in drilling, production, transporting, and refining of crude oil. Can be formulated with inorganic and organic acids to form liquid, water-soluble salts for use as corrosion preventives, emulsifiers, wetting agents, or scale preventives. Highly cationic amine that can be used in concentrated form or diluted for application purposes.

CI-821 (CE-72) - 98 to 100% active amido imidazoline derived from monobasic acids to formulate corrosion inhibitors for use in drilling, production, transporting, and refining of crude oil. Can be formulated with inorganic and organic acids to form liquid, water-soluble salts for use as corrosion preventives, emulsifiers, wetting agents, or scale preventives.

Alpha 2290 - 98 to 100% active alkyl phosphate ester, acid form, designed as a corrosion inhibitor for use in water injection systems. Anodic inhibitor that controls general and pitting corrosion for oxygen, hydrogen sulfide, and carbon dioxide. Should be maintained at concentrations of 500-2000 ppm in most systems.

Alpha 2296 - 52 to 58% active potassium salt of a glycol phosphate ester designed as a corrosion inhibitor for use in water injection systems. Anodic inhibitor that controls general and pitting corrosion for oxygen, hydrogen sulfide, and carbon dioxide. Should be maintained at concentrations of 500-2000 ppm in most systems.

Alpha 3385 - 61 to 65% active amine salt of poly-phosphate ester that functions as a combination oil-soluble scale and corrosion inhibitor additive. Also functions as a refinery antifoulant and corrosion inhibitor for product pipelines. Can be used in concentrated form or diluted with hydrocarbon solvents or oil for application purposes.

Alpha 3220 - 70 to 75% active soluble organic-boron amine solution used to prepare corrosioninhibitors for oxygen, carbon dioxide, hydrogen sulfide, organic and mineral acids, and dissolvedsalts for applications in oil, gas, or water well producing systems and in water injection systems.Can be diluted with water, water-alcohol, or water-glycol solutions for application purposes.

CI-810 (CE-86) - 100% active tallow diamine ethoxylate (10 moles of EO) used as an extremely versatile corrosion inhibitor base with high detergent properties. Used in both water-soluble and oil soluble formulations and is a strong film forming agent.

Alpha 3356 - 70 to 75% active complex fatty acid-amine salt used to formulate thermally stable corrosion preventives for applications in drilling, production, transporting, and refining of crude oil. Used as a corrosion prevention additive in oil systems, water floods, and water disposal systems. Can be used in concentrated form or diluted with hydrocarbon solvents, isopropanol, or water-isopropanol solutions for application purposes.

Alpha 3370 - 88 to 90% active polyacid, organic acid-polyamide salt with quaternary ammonium chloride used as a corrosion inhibitor in drilling, producing, transporting, and refining of crude oil. Functions as corrosion preventive and anti-foulant in oil systems, water floods, and water disposal systems. Can be used in concentrated form or diluted (20-50% by volume) with hydrocarbon solvents for application purposes. Alpha 7370 is a 30% dilution of Alpha 3370 to yield a 25 to 29% active product in a hydrocarbon solvent. Alpha 7420 is a 22% dilution of Alpha 3370 to yield a 18 to 22% active product in a hydrocarbon solvent.

Alpha 3456 - 12 to 16% active amine salt of polyphosphonic acid designed as an oil-soluble scale inhibitor for water systems. Contains cationic amines to create a combination scale and corrosion prevention product that is thermally stable in excess of 350° F. (177° C.). Can be diluted with hydrocarbon solvents or oil.

Alpha 3488 - 75 to 80% active organic acid-amine salt used to formulate non-emulsifying corrosion inhibitors for use in drilling, producing, transporting, and refining of crude oil. Can be used in concentrated form or diluted (20 to 35% by volume) with hydrocarbon solvents for application purposes.

Alpha 3489 - 75 to 80% active organic acid-amine salt used to formulate corrosion inhibitors for use in drilling, producing, transporting, and refining of crude oil. Used as corrosion and scale preventives in oil systems, water floods, or water disposal systems. Can be used in concentrated form or diluted with hydrocarbon solvents.

Alpha 3732C - 95 to 99% active organic acid-amine salt used to formulate thermally stable corrosion inhibitors for use in drilling, producing, transporting, and refining of crude oil. Used in oil and gas wells, oil transport systems, refineries, and water flood or disposal systems. Can be used in concentrated form or diluted with hydrocarbon solvents, aromatic or aliphatic, for application purposes. Effective against carbon dioxide, hydrogen sulfide, and oxygen.

Alpha 3930 - 98 to 100% active crude dimerized fatty acid to formulate corrosion preventives for use in drilling, producing, transporting, and refining of crude oil. Can be formulated with amides, amines, or imidazolines for use as corrosion preventives, emulsifiers, wetting agents, or scale preventives. Can be used in concentrated form or diluted for application purposes in all types of oil systems.

CI-850 (CE-1050) - Tall oil dimer-trimer acid that is typically blended with imidazolines, amides, and other amine-based corrosion inhibitors extend film life and provide corrosion control properties in both sweet and sour environments.

Crude oil contains natural surfactants, which, when mixed with water, can emulsify the water into oil. The more common emulsion is water dispersed in oil, but "reverse" emulsions (oil in water) can also occur. Emulsions raise the bottom sediment and water (BS and W) of oil and are often very viscous. Emulsion breakers are a class of chemicals used to separate emulsions (e.g. water in oil). They are commonly used in the processing of crude oil, which is typically produced along with significant quantities of saline water. This water (and salt) must be removed from the crude oil prior to refining. If the majority of the water and salt are not removed, significant corrosion problems can occur in the refining process. Emulsion breakers are typically based on the following chemistry: acid catalysed phenol-formaldehyde resins; base catalyzed; phenol-formaldehyde resins; epoxy resins; polyethyleneimines; polyamines; di-epoxides; or polyols. Commercially available emulsion breakers are sold by Weatherford, such as those described in Table 2 below.

TABLE 2

DB-904 - Amine-based demulsifier that provides a clean interface and clean water. More effective on mid-range API gravity crudes, than poly-based products. Can be used to treat oil-in-water emulsions. The relative solubility number (RSN) is 12.5.

DB-951 - Amine-based demulsifier that provides a clean interface and clean water. More effective on mid-range API gravity crudes, than poly-based products. Can be used to treat oil-in-water emulsions. The relative solubility number (RSN) is 10.0.

DB-954 - Amylresin-based demulsifier that is effective in mixed and asphaltenic crudes. Effective in low to high gravity API crudes to provide primary water drop and drop entrained water. The relative solubility number (RSN) is 11.3.

DB-955 - Amyl resin-based demulsifier that is effective in mixed and asphaltenic crudes. Effective in low to high gravity API crudes to provide primary water drop and drop entrained water. The relative solubility number (RSN) is 14.5.

TABLE 2-continued

DB-958 - Amyl resin-based demulsifier that is effective in mixed and asphaltenic crudes. Effective in low to high gravity API crudes to provide primary water drop and drop entrained water. The relative solubility number (RSN) is 16.0.

DB-942 - Butyl resin-based demulsifier that is effective in paraffinic and mixed crudes. Effective in low to high gravity API crudes to provide primary water drop and drop entrained water. The relative solubility number (RSN) is 9.5.

DB-945 - Butyl resin-based demulsifier that is effective in paraffinic and mixed crudes. Effective in low to high gravity API crudes to provide primary water drop and drop entrained water. The relative solubility number (RSN) is 9.0.

DB-934 - Nonyl resin-based demulsifier that is effective in naphthenic crudes. Effective in low to high gravity API crudes to provide primary water drop and drop entrained water. Nonyl resins are the most widely used on a global basis. The relative solubility number (RSN) is 15.0.

DB-935 - Nonyl resin-based demulsifier that is effective in naphthenic crudes. Effective in low to high gravity API crudes to provide primary water drop and drop entrained water. Nonyl resins are the most widely used on a global basis. The relative solubility number (RSN) is 16.5.

DB-946 - Nonyl resin-based demulsifier that is effective in naphthenic crudes. Effective in low to high gravity API crudes to provide primary water drop and drop entrained water. Nonyl resins are the most widely used on a global basis. The relative solubility number (RSN) is 10.5.

DB-947 - Nonyl resin-based demulsifier that is effective in naphthenic crudes. Effective in low to high gravity API crudes to provide primary water drop and drop entrained water. Nonyl resins are the most widely used on a global basis. The relative solubility number (RSN) is 13.5.

Alpha 4068 - 60 to 65% active polymerized resin-ester-blend that functions as a demulsifier intermediate used to prepare formulas for treating crude oil emulsions at wellheads, tank batteries, or other gathering points. Also used to prepare solutions for desalting of crude oil. Should be diluted with heavy aromatic naphtha, xylene, or other aromatic solvents for improved performance.

Alpha 4212 - 94 to 98% active triol fatty acid ester that functions as a demulsifier intermediate used to prepare formulas for treating crude oil emulsions at wellheads, tank batteries, or other gathering points. Also used to prepare solutions for desalting of crude oil. Should be diluted with heavy aromatic naphtha, xylene, or other aromatic solvents for improved performance.

Alpha 4312 - 83 to 87% active triol adipate ester that functions as a demulsifier intermediate used to prepare formulas for treating crude oil emulsions at wellheads, tank batteries, or other gathering points. Also used to prepare solutions for desalting of crude oil. Should be diluted with heavy aromatic naphtha, xylene, or other aromatic solvents for improved performance.

Alpha 4531 - 100% active triol fumarate ester that functions as a demulsifier intermediate used to prepare formulas for treating crude oil emulsions at wellheads, tank batteries, or other gathering points. Also used to prepare solutions for desalting of crude oil. Should be diluted with heavy aromatic naphtha, xylene, or other aromatic solvents for improved performance.

DB-918 - Polyolester-based demulsifier used to treat loose emulsions providing a clean interface and clean water. The relative solubility number (RSN) is 7.5.

DB-911 - Polyol-based demulsifier used to treat loose emulsions providing a clean interface and clean water. The relative solubility number (RSN) is 10.8.

DB-938 - Polyol-based demulsifier used to treat loose emulsions providing a clean interface and clean water. The relative solubility number (RSN) is 9.9.

DB-961 - Polyol-based demulsifier used to treat loose emulsions providing a clean interface and clean water. The relative solubility number (RSN) is 13.3.

DB-964 - Polyol-based demulsifier used to treat loose emulsions providing a clean interface and clean water. Water-wets the solids, dropping them to the water phase. Also used in desalter formulations. The relative solubility number (RSN) is 17.5.

DB-984 - Polyol-based demulsifier used to treat loose emulsions providing a clean interface and clean water. Water-wets the solids, dropping them to the water phase. Also used in desalter formulations. The relative solubility number (RSN) is 20.0.

Alpha 2618 - 55 to 60% active ammonium sulfonate used to prepare emulsion preventives for oil washes, removal of mud blocks, water blocks and emulsion blocks, and in workovers and chemical treatments. Usually diluted with water, xylene, methanol, or other alcohols.

Alpha 4153 - 90 to 95% active isopropylamine sulfonate that is used to prepare emulsion preventives for oil washes, removal of mud blocks, water blocks and emulsion blocks, and in workovers and chemical treatments. Usually diluted with water, methanol, xylene, or alcohols.

Alpha 4180 - 65 to 70% active amine sulfonate used to prepare emulsion preventives for oil washes, removal of mud blocks, water blocks and emulsion blocks, and workovers and chemical treatments. Also functions as a dispersant for paraffin removal. Usually diluted with heavy aromatic naphtha, xylene, or alcohols.

Alpha 2919 - 98 to 100% active ethoxylated fatty oil that is used to formulate surfactants for water floods or water disposal systems to clean solids, oil, and lower interfacial tension of oil and water to formation rock. Usually diluted in water, alcohols, or aromatic solvents for applications.

Alpha 4122 - 63 to 68% active polymerized resin ester of phenolic with an acrylate-anhydride polyglycol polymer that functions as a demulsifier intermediate used to prepare formulas for treating crude oil emulsions at wellheads, tank batteries, or other gathering points. Also used to prepare solutions for desalting crude oil. Should be diluted with heavy aromatic naphtha, xylene, or other aromatic solvents for improved performance.

Alpha 4138 - 85 to 90% active blend of amine sulfonates, polyglycols, ketone, and terpene used to prepare emulsion preventives for oil washes, removal of mud blocks, water blocks and emulsion blocks, and in workovers and chemical treatments. Usually diluted with xylene, alcohol, or aromatic naphthas.

Alpha 4400 - 80 to 85% active complex mixture of amine sulfonates and polyglycols used to prepare emulsion preventives for oil or water washes and for the prevention of emulsions in workovers or chemical treatments. Usually diluted with heavy aromatic naphtha, xylene, or alcohols.

Alpha 4670 - 40 to 45% active blend of polymerized polyglycol and an oxyalkylated alkyl phenolic resin terminated polyurea of a triol that functions as a demulsifier intermediate used to prepare formulas for treating crude oil emulsions at wellheads, tank batteries, or other gathering points. Also used to prepare solutions for desalting crude oil. Should be diluted with heavy aromatic naphtha, xylene, or other aromatic solvents for improved performance.

ALPHA-BREAK (emulsion breaker, Weatherford) 105 - Oil-soluble demulsifying surfactant containing an ammonium salt of a naphthalene sulfonate in aromatic solvents that effectively "breaks" oilfield emulsions. Proper concentration can be determined based on a relatively simple bottle test.

ALPHA-BREAK 400 (emulsion breaker, Weatherford) - Oil-soluble demulsifying surfactant containing an ammonium salt of a naphthalene sulfonate, with an ethoxylated resin in aromatic solvents that effectively "breaks" oilfield emulsions. Usually 30 to 500 ppm is recommended, but the proper concentration can be determined based on a relatively simple bottle test.

DB-928 - Specialty blend demulsifier that speeds water drop and allows treatment at lower temperature and lower rates when used in combination with other demulsifiers. The relative solubility number (RSN) is 5.5.

DB-937 - Specialty blend demulsifier that speeds water drop and allows treatment at lower temperature and lower rates when used in combination with other demulsifiers. The relative solubility number (RSN) is 7.8.

TABLE 2-continued

DB-939 - Specialty blend demulsifier that speeds water drop and allows treatment at lower temperature and lower rates when used in combination with other demulsifiers. The relative solubility number (RSN) is 9.9.
DB-941 - 40 to 45% active blend of phenol formaldehyde resin and polyamine that functions as a demulsifier for treating crude oil emulsions at
wellheads, tank batteries, or other gathering points. Speeds the water drop from the emulsion and allows treatment at lower temperatures. Can be used in
combination with other demulsifiers. The relative solubility number (RSN) is
12.5.
DB-9393 - Specialty blend demulsifier that speeds water drop and allows treatment at lower temperature and lower rates when used in combination with other demulsifiers. The relative solubility number (RSN) is 5.0.
DC-903 - Concentrated alkoxylated alkylphenol formaldehyde resin blend that functions as a desalter and demulsifier for medium to high gravity crude
oils. Usually diluted 2 to 3 times in solvents and applied at concentrations from 10 to 50 ppm.
DC-904 - Concentrated alkoxylated alkylphenol formaldehyde resin blend that functions as a desalter and demulsifier for low to medium gravity crude
oils. Usually diluted 2 to 3 times in solvents and applied at concentrations from 10 to 50 ppm.
DC-905 - Concentrated alkoxylated alkylphenol formaldehyde resin blend that functions as a desalter and demulsifier for medium to high gravity crude
oils. Usually diluted 2-3 times in solvents and applied at concentrations from
10-50 ppm.
DC-907 - Concentrated alkoxylated alkylphenol formaldehyde resin blend that functions as a desalter and demulsifier for low to medium gravity crude
oils. Usually diluted 2-3 times in solvents and applied at concentrations from
10-50 ppm.

Hydrogen Sulfide ($H_2S$) is a poisonous gas that is deadly at high concentrations and poses serious health threats at moderate concentrations. Operating problems caused by $H_2S$ can include severe corrosion and fouling, and injection-well plugging with iron sulfides. Hydrogen sulfide controllers are a class of compounds that react with $H_2S$ to convert the $H_2S$ or mercaptans into other sulfur compounds. Exemplary hydrogen sulfide controllers are oxidizers, such as peroxide, amine neutralizers, sodium hydroxide or a blend of sodium and potassium hydroxide, triazine-based chemistry, metal scavengers, etc. Commercially available hydrogen sulfide controllers are sold by Weatherford, such as those described in Table 3 below.

TABLE 3

Alpha ONE - A 50 to 55 percent active aqueous, polymeric, amino-alcohol solution designed to be effective in drilling-fluid systems as both a $H_2S$ converter and corrosion inhibitor. Temperature stable, it can be used as an additive in acid stimulation treatments. The scavenging rate in a liquid mud
system is 2.0 to 75.0 ppm per ppm sulfide.
SULFACLEAR 8199 (hydrogen sulfide controller, Weatherford) - A72 to 76
percent active, oil-soluble, cyclic, tertiary amine designed as a $H_2S$ scavenger
for gas systems. It can be diluted with aromatic solvents, diesel, kerosene or
other low-molecular-weight alcohols. The scavenging rate is 1.0 to 5.0 ppm
per ppm $H_2S$ in gas systems.
SULFACLEAR 8211 (hydrogen sulfide controller, Weatherford) - A33 percent active, aqueous, cyclic, tertiary amine solution designed as a sulfide
scavenger for gas and water. The scavenging rate in gas is 1.0 to 8.0 ppm per
ppm sulfide. In water-based systems, the ratio is 6.0 to 15.0 ppm per ppm $H_2S$. It can be diluted with methanol or water for application purposes.

TABLE 3-continued

SULFACLEAR 8250 (hydrogen sulfide controller, Weatherford) - A33 percent active, aqueous amine solution designed as a sulfide scavenger for gas and water. The scavenging rate in gas is 1.0-8.0 ppm per ppm sulfide. In
water based systems the ratio is 6.0 to 15.0 ppm per ppm $H_2S$. It can be diluted with methanol or water for application purposes.
SULFACLEAR 8311 (hydrogen sulfide controller, Weatherford) - A 47 percent active, aqueous cyclic tertiary amine solution designed as a sulfide scavenger for gas treating applications. This solution is ideally suited for treating gas with high $CO_2$ concentrations.
SULFACLEAR 8411C (hydrogen sulfide controller, Weatherford) - A 50 percent active, aqueous, cyclic, tertiary amine solution designed as a sulfide
scavenger for water. The scavenging rate in water systems is 2.0 to 20.0 ppm
per ppm sulfide. For treatment of $H_2S$ in gas or crude oil, concentrations range from 1.0 to 10.0 ppm per ppm $H_2S$. It can be diluted with water or methanol.
SULFACLEAR 8411HC (hydrogen sulfide controller, Weatherford) - An 80
percent active, aqueous, cyclic, tertiary amine designed as a sulfide scavenger
for water. The scavenging rate in water systems is 2.0 to 20.0 ppm per ppm
sulfide. This solution is used for treatment of $H_2S$ in gas concentrations range
from 1.0 to 10.0 ppm per ppm $H_2S$. It can be diluted with water or methanol.
SULFACLEAR 8419 (hydrogen sulfide controller, Weatherford) - A 47 percent active, aqueous, cyclic, tertiary amine solution designed as a sulfide
scavenger for gas treating applications. This solution is ideally suited for treating gas with high $CO_2$ concentrations. Usually used in bubble tower applications, it has a scavenging rate of 3.0 to 10.0 ppm per ppm sulfide.
SULFACLEAR 8495 (hydrogen sulfide controller, Weatherford) - A 63 percent active, aqueous, cyclic, tertiary amine benzyl quaternary blended compound solution designed as a $H_2S$ scavenger and water clarifier. The scavenging rate in water systems is 2.0 to 20.0 ppm per ppm $H_2S$.
SULFACLEAR 8640 (hydrogen sulfide controller, Weatherford) - A patented, 50 percent active, aqueous, cyclic, tertiary, amine polymer blend containing surfactants designed as a $H_2S$ and mercaptan scavenger for water
or gas systems. The scavenging rate is 1.0 to 4.0 ppm per ppm $H_2S$. It can be
diluted with methanol, glycols or water.
SULFACLEAR 8640HC (hydrogen sulfide controller, Weatherford) - An 80
percent active, aqueous, cyclic, tertiary amine polymer blend containing surfactants designed as a $H_2S$ scavenger for water or gas systems. The scavenging rate is 1.0 to 4.0 ppm per ppm $H_2S$. It can be diluted with methanol, glycols, or water.
SULFACLEAR 8649 (hydrogen sulfide controller, Weatherford) - A patented, 50 percent active, aqueous, cyclic, tertiary amine polymer-blend resin solution that contains surfactants and functions as a $H_2S$ and mercaptan
scavenger for water or gas systems. The scavenging rate is 1.0 to 4.0 ppm per
ppm $H_2S$ in water systems, and 4.0 to 20.0 ppm per ppm $H_2S$ in gas systems.
It can be diluted with methanol, glycols or water.
SULFACLEAR 8849 (hydrogen sulfide controller, Weatherford) - A 100 percent active, oil-soluble alkyl amine-formaldehyde condensate that functions as a $H_2S$ scavenger for gas, oil and multiphase systems. The scavenging rate is 1.0 to 5.0 ppm per ppm $H_2S$. It can be diluted with aromatic solvents, diesel, kerosene or other low-molecular-weight alcohols.

Most crude oils contain paraffin in solution, and cooling causes paraffin crystals to clump together and build up on production equipment. Left untreated, the buildup will eventually shut off the flow of oil by completely plugging tubing and flow lines. Paraffin control additives are a class of compounds that help prevent or minimize the amount of paraffin deposits formed. Commercially available hydrogen sulfide controllers are sold by Weatherford, such as those described in Table 4 below.

TABLE 4

Alpha 5242 - 40% active acidic copolymer in aromatic naphtha that functions
as a wax crystal modifier for crude oils and heavy fuel oils. Can be used neat
or diluted (20% by volume) with heavy aromatic naphtha, toluene, or xylene
for continuous or batch injection. Normally applied at concentrations of 100
to 2000 ppm to crude above its crystallization point or heated and mixed.
Alpha 5445 - 95 to 100% active alkylated polyester amide, copolymer, and
wax composition that functions as a pour point depressant for crude oils and
heavy oils. Can be used neat, when hot, or diluted with heavy aromatic
naphtha, toluene, or xylene for continuous or batch injection. Normally
applied at concentrations of 100 to 2000 ppm to crude above its
crystallization point or heated and mixed.
Alpha 5482 - 73 to 77% active alkylated polyester in xylene that functions as
a wax crystal modifier for crude oils and heavy fuel oils. Can be used neat or
diluted with heavy aromatic naphtha, toluene, or xylene for continuous or
batch injection. Normally applied at concentrations of 100 to 2000 ppm to
crude above its crystallization point or heated and mixed.
Alpha 5603C - 100% active alkylated polyester that functions as a wax
crystal modifier for crude oils and heavy fuel oils. Can be diluted (20% by
volume) with heavy aromatic naphtha, toluene, or xylene for continuous or
batch injection. Normally applied at concentrations of 100 to 2000 ppm to
crude above its crystallization point or heated and mixed.
Alpha 5609 - 40% active alkylated polyester amide/imide that functions as a
wax crystal modifier for crude oils and heavy fuel oils. Can be used neat or
diluted with heavy aromatic naphtha, toluene, or xylene for continuous or
batch injection. Normally applied at concentrations of 100 to 2000 ppm to
crude above its crystallization point or heated and mixed.
Alpha 7526 - 40% active amine sulfonate mixture used as a pour point
depressant to disperse and remove paraffin. Can be used in its concentrated
form or diluted with heavy aromatic naphtha, diesel fuel, xylene, or alcohols
for ease of handling. Can be used in pipelines, producing wells, oil handling
and storage equipment, and in refineries.
Alpha 7527 - 30% active amine sulfonate mixture used as a pour point
depressant to disperse and remove paraffin. Can be used in its concentrated
form or diluted with heavy aromatic naphtha, diesel fuel, xylene, or alcohols
for ease of handling. Can be used in producing wells, oil handling and
storage equipment, and in refineries.
PARA CLEAR D290 (Paraffin control additive, Weatherford) - Contains
synergistic blends of surfactants, amines, alcohols and diols to not only
penetrate and disperse the paraffin, but also isolate the paraffin molecules by
forming a coating around them to inhibit their growth. Should be mixed at 3
to 10% in fresh water, pumped down the casing annulus, and allowed to
contact the paraffin for 12 to 24 hours.
PARA CLEAR D500 (Paraffin control additive, Weatherford) - Contains
synergistic blends of surfactants, amines, alcohols and diols to not only
penetrate and disperse the paraffin, but also isolate the paraffin molecules by
forming a coating around them to inhibit their growth. Should be mixed at 10
to 15% in fresh water and allowed to contact the paraffin for 12 to 24 hours.
PARA CLEAR D700 (Paraffin control additive, Weatherford) - Synergistic
blend of surfactants and amines in an environmentally friendly fluid that not
only disperses paraffin molecules, but also inhibits their growth. Contains no
BTX solvents and is normally mixed at 10 to 15% by volume in fresh water.
PARA CLEAR HWD-106 (Paraffin control additive, Weatherford) -
Composed of ionic and non-ionic components mixed in selective solvents to
remove accumulated paraffin deposits while preventing the paraffin from
separating out of the oil phase. Leaves the surface of the pipe "water-wet",
thus retarding the re-deposition of paraffin for a period of time. Should be
mixed at 10 to 15% in fresh water and allowed to contact the paraffin for 12
to 24 hours.

TABLE 4-continued

ParaClean 26 - Amine sulfonate mixture used to disperse and remove paraffin
deposits in pipelines, gathering systems, oil handling and storage equipment,
and in refineries. Can be used in its concentrated form or can be diluted with
heavy aromatic naphtha, diesel fuel, xylene, or alcohols for ease of handling.
Particularly effective in pipeline pigging operations as a single step product.
ParaClean 27C - Amine sulfonate mixture used to dissolve, disperse and
remove paraffin deposits in pipelines, gathering systems, oil handling and
storage equipment, and in refineries. Can be used in its concentrated form or
can be diluted with heavy aromatic naphtha, diesel fuel, xylene, or alcohols
for ease of handling. Most effective when used in a continuous treatment
alone or in advance of a pigging procedure.
PD-816 - 100% active blend of amines, alcohols, and sulfonates used to
formulate both oil- and water-soluble paraffin dispersants to treat paraffenic,
asphaltenic, and/or naphthenic crude oil production.

Scale occurs because the minerals in produced water exceed their saturation limit as temperatures and pressures change. Scale can vary in appearance from hard crystalline material to soft, friable material and the deposits can contain other minerals and impurities such as paraffin, salt and iron. The most common of the mineral scales is calcium carbonate. Other common mineral deposits include calcium sulfate (gypsum), strontium sulfate, and barium sulfate. Scale inhibitors are used to prevent these deposits from forming. There are three common types of chemical compounds used for this purpose, phosphate esters, phosphonates, and acid polymers. Commercially available hydrogen sulfide controllers are sold by Weatherford, such as those described in Table 5 below.

TABLE 5

Alpha 2003 and Alpha 2004 - are concentrated 95- to 100-percent active
alkyl-nonylphenol-phosphate-ester-acid anionic surfactants with
multifunctional abilities. They can be formulated to perform as an emulsifier,
wetting agent, antifoulant, cleaner, or detergent. These products can be used
in foam and air-mist drilling systems without offsetting drilling fluid
properties.
Alpha 2401 - is a 40- to 45-percent active bishexamethylenetriamine
pentamethylene phosphonic acid sodium salt concentrate used to formulate
scale preventives for treatment of calcium carbonate, calcium, barium, and
strontium sulfate.
Alpha 2240 - is a 70- to 80-percent active hydroxyamino phosphate ester
concentrate used to formulate scale preventives for squeeze or continuous
treatment of calcium carbonate, calcium, barium, and strontium sulfate.
Alpha 2240-70 - is a 57- to 61-percent active hydroxyamino phosphate ester
concentrate used to formulate scale preventives for squeeze or continuous
treatment of calcium carbonate, calcium, barium, and strontium sulfate.
Alpha 2247 is a 63- to 67-percent active hydroxyamino phosphate ester
sodium salt concentrate used to formulate scale preventives for treatment of
calcium carbonate, calcium, barium, and strontium sulfate.
Alpha 2290 - is a 90- to 100-percent active alkyl phosphate ester acid
corrosion preventive used in water-based drilling systems.
Alpha 2408 - is a 35- to 45-percent active sodium salt of a modified diamine
phosphonate concentrate used to formulate scale preventives.
Alpha 2801 - is a 48- to 52-percent active bishexamethylenetriamine
pentamethylene phosphonic acid used as a concentrate for treating calcium
and magnesium carbonate, calcium, barium, and strontium sulfate.
Alpha 2803 - is a 48- to 52-percent active diethylenetriamine pentamethylene
phosphonic acid to formulate scale preventives for treatment of calcium and
magnesium carbonate, calcium sulfate, and barium scales.

TABLE 5-continued

Alpha 2807 - is a 48- to 52-percent active concentrate of phosphonate and ether diamines, triamines, and tetramines used to formulate scale preventives
for treating calcium and magnesium carbonate, calcium, barium, strontium sulfate, and iron scales.
Alpha 2867 - is a 38- to 42-percent active ammonium salt of ether diamine,
triamine, and tetramine phosphonate, used to formulate scale preventives for
treatment of calcium and magnesium carbonate, calcium, barium, strontium
sulfate, and iron scales.
Alpha 2771 - 50 to 55% active sodium salt of complex polyacrylate designed
as a scale inhibitor for calcium and magnesium carbonate, calcium, barium and strontium sulfate, and iron scales in water systems. Also functions as a
dispersant and sludge conditioner in boilers. Can be diluted with water or water and antifreeze agents before use for ease of handling.
J-Poly 101A - 50% active polyacrylate scale inhibitor. Effective against calcium carbonate, calcium sulfate, and certain iron scales. Stable at high temperatures and is slightly acidic (pH 3-4).
SCALECLEAR A100 (Scale inhibitor, Weatherford) - is a liquid blend containing both organic and mineral acids, corrosion inhibitors, and amphoteric surfactants used to dissolve carbonate, iron-sulfide, and iron-oxide scales.
SCALECLEAR CSP (Scale inhibitor, Weatherford) - is a solid controlled-release scale preventive containing three formulations of fused sodium-calcium phosphate glass, each with a guaranteed minimum phosphorus pentoxide content of 68 percent, designed for treatment of calcium carbonate,
calcium, barium, and strontium sulfate.
NA-MINUS 55 (Scale inhibitor, Weatherford) - Liquid formulation of imido
polyalkyl amides used to inhibit precipitation of sodium chloride salt from high chloride brines. Allows treatment fluids to carry very high salt saturations up to 40%. Generally, 5% by volume of fresh water is recommended for batch treatments. For continuous treatment, 250 to 1000 ppm (parts per million) neat chemical should be added to the brine.
NA-MINUS (Scale inhibitor, Weatherford) - Liquid formulation of amino acid amides that controls salt deposition over the wide temperature and pressure ranges encountered from the bottom of the hole to the surface in producing wells. Dosage requirements will vary with brine, temperature changes, solids concentration, pH and equilibrium time. For continuous treatment, 250 to 1000 ppm (parts per million) neat chemical should be added
to the brine.

Aspects of the invention are accomplished using a porous substrate spray ionization probe coupled to a mass spectrometer, such as a miniature mass spectrometer. In certain embodiments, the miniature mass spectrometer includes a discontinuous atmospheric pressure interface (DAPI), which is discussed in greater detail below. In certain embodiments, the porous substrate spray probe coupled to a mass spectrometer is used to analyze, identify, and quantify analytes (e.g., corrosion inhibitors) in crude oil. Porous substrate spray allows the analysis to occur without any sample preparation or pre-purification. In methods of the invention, crude oil is taken from a source, e.g., a pipeline, and in an unmodified form, is spotted directed onto the paper spray probe. Such a set-up is exemplified in FIG. 1. Solvent is applied and the spray generated from the paper probe is analyzed (FIG. 1).

Methods of the invention can be conducted in an ambient environment and allow for ambient ionization mass spectrometry of crude oil samples, i.e., ionization is performed on unmodified samples in air. This approach provides almost instantaneous data while eliminating or minimizing sample preparation or sample pre-purification. Accordingly, methods of the invention allow for rapid and efficient in-field techniques for analyzing an analyte in crude oil, such as monitoring of corrosion inhibitors in the oil in transmission pipelines. Ambient ionization is described for example in Nemes et al. (Trends in Anal. Chem., 2012, 34, 22-34), Harris et al. (Anal. Chem., 2011, 83, 4508-4538), Huang et al., (Ann. Rev. Anal. Chem., 2010, 3, 43-65), Ifa et al. (Analyst, 2010, 135, 669-681), Cooks et al. (Science, 2006, 311, 1566-1570, Cooks et al. (Faraday Discussions, 2011, 149, 247-267), Venter et al. (Anal. Chem., 2008, 27, 284-290), Harris et al. (Analyst, 2008, 133, 1297-1301), Takats et al. (Science, 2004, 306, 471-473), Cody et al. (Anal. Chem., 2005, 77, 2297-2901), and Ratcliffe et al. (Anal. Chem., 2007, 79, 6094), the content of each of which is incorporated by reference herein in its entirety.

Porous substrate spray is further described in Ouyang et al. (U.S. patent application serial number 2012/0119079), the content of which are incorporated by reference herein in its entirety. The paper spray ionization method is soft (it deposits little internal energy into ions) and amenable to the analysis of small and large molecules ranging from simple organics to large biomolecules (Wang et al., Angew Chemie-International Edition., 2010, 49, 877-880; Zhang et al., Anal. Chem., 2012, 84(2) 931-938; Yang et al., Anal & Bio. Chem., 2012, 404, 1389-1397, and Zhang et al., Analyst, 2012, 137, 2556-2558).

In the porous substrate spray embodiment, the sample is spotted onto a porous substrate, e.g., paper (or other solid medium). The porous substrate may be cut to a fine point. In certain embodiments, the porous substrate tapers to a microscopic tip, such as a carbon nanotube. The porous substrate is wetted with solvent and charged liquid droplets are emitted from the porous substrate tip when a high DC voltage (±3.5 kV) is applied. Without being limited by any particular theory or mechanism of action, it is believed that droplet emission occurs by field emission (Espy et al., Int. J. Mass Spectrom, 2012, 325-327, 167-171). Subsequent ion generation from the charged droplets is thought to follow electrospray-like mechanisms (Crotti et al., Euro. J. Mass Spectrom, 2011, 17, 85-99). Porous substrate ionization is described in greater detail below.

In certain embodiments, porous substrate spray ionization is combined with a portable mass spectrometer for rapid, in-situ analysis of corrosion inhibitor actives (i.e. alkyl ammonium salts) in petroleum oil. It is believed that tetra-dodecylammonium bromide and benzylhexadecyldimethyl-ammonium chloride are representative of the active components in many corrosion inhibitor formulations (Quraishi et al., Am. Oil Chem. Soc., 2000, 77, 1107-1111, Treybig et al., U.S. Pat. No. 4,957,640, Derek et al., U.S. Pat. No. 4,235, 838, and Young et al., U.S. Pat. No. 6,645,399). Both compounds contain long hydrophobic alkyl chains that allow them to dissolve in oil. The data in the Example below show that <1 ng/μL of quaternary ammonium salt in 1 μL oil (e.g., pump oil) placed onto paper can be detected easily using either a commercial bench-top or a miniature mass spectrometer. This concentration (<100 ppb) of the active corrosion inhibitor is well below the reported minimum effective range of concentrations of these inhibitors, which is 50-200 ppm (Viswanathan, Corrosion Science, 2010, 2, 6-12; and Boris et al., NACE International Corrosion Conference and Exponent, 2009, No 09573). The data further demonstrate that in-situ analyte(s) identification was achieved by analyzing the fragmentation patterns of the corrosion inhibitors generated using tandem mass spectrometry (MS/MS; Jackson et al., Eur. Mass Spectrom., 1997, 3, 113-120; Jackson et al., Int. J. Mass Spectrom., 2004, 238, 265-277; Jackson et al., Rapid Commun. Mass Spectrom., 2006, 20, 2717-2727; (Busch et al., Mass Spectrometry/Mass Spectrometry: Techniques and applications of Tandem Mass Spectrometry, VCH Publishers Inc., New York, 1988).

Miniature Mass Spectrometers

As mentioned above, the mass spectrometer may be for a bench-top or lab-scale mass spectrometer or a miniature mass spectrometer. An exemplary miniature mass spectrometer is described, for example in Gao et al. (Z. Anal. Chem. 2006, 78, 5994-6002), the content of which is incorporated by reference herein in its entirety In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety. Miniature mass spectrometers are also described, for example in Xu et al. (JALA, 2010, 15, 433-439); Ouyang et al. (Anal. Chem., 2009, 81, 2421-2425); Ouyang et al. (Ann. Rev. Anal. Chem., 2009, 2, 187-214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082).), the content of each of which is incorporated herein by reference in its entirety.

Ionization Using Wetted Porous Material

Figure 14A:
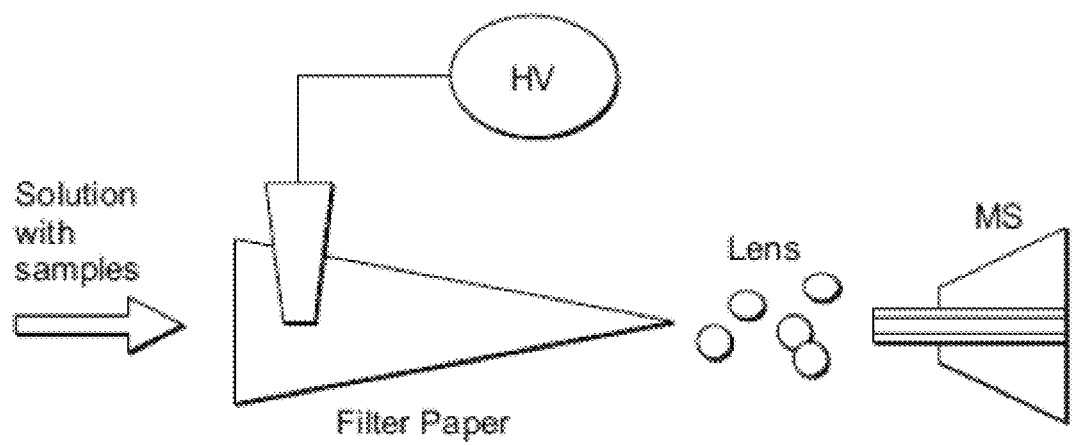
FIG. 14A shows a schematic of a sample solution being fed to a piece of paper for electrospray ionization.
Figure 14B:
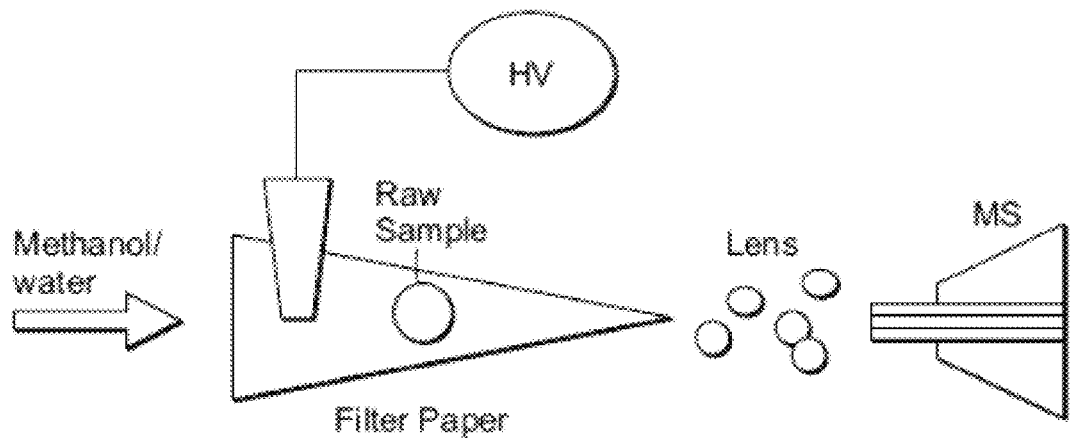
FIG. 14B shows a schematic of a sample, such as crude oil, pre-spotted onto the paper and a droplet of solvent being subsequently supplied to the paper for electrospray ionization.

Probes comprised of porous material that is wetted to produce ions are described in Ouyang et al. (U.S. patent application number 2012/0119079 and PCT application number PCT/US10/32881), the content of each of which is incorporated by reference herein in its entirety. Exemplary probes are shown in FIGS. 14A-B. Porous materials, such as paper (e.g. filter paper or chromatographic paper) or other similar materials are used to hold and transfer liquids and solids, and ions are generated directly from the edges of the material when a high electric voltage is applied to the material. The porous material is kept discrete (i.e., separate or disconnected) from a flow of solvent, such as a continuous flow of solvent. Instead, sample is either spotted onto the porous material or swabbed onto it from a surface including the sample. The spotted or swabbed sample is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 µm), Grade 2 (8 µm), Grade 595 (4-7 µm), and Grade 6 (3 µm). Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultrafiltration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 µm or wider, at least about 10 µm or wider, at least about 50 µm or wider, at least about 150 µm or wider, at least about 250 µm or wider, at least about 350 µm or wider, at least about 400µ, or wider, at least about 450 µm or wider, etc. In particular embodiments, the tip width is at least 350 µm or wider. In other embodiments, the probe tip width is about 400 µm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples. Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples. In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper.

In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds. Hydrophobic regions may be patterned onto paper by using photolithography, printing methods or plasma treatment to define hydrophilic channels with lateral features of 200~1000 µm. See Martinez et al. (Angew. Chem. Int. Ed. 2007, 46, 1318-1320); Martinez et al. (Proc. Natl Acad. Sci. USA 2008, 105, 19606-19611); Abe et al. (Anal. Chem. 2008, 80, 6928-6934); Bruzewicz et al. (Anal. Chem. 2008, 80, 3387-3392); Martinez et al. (Lab Chip 2008, 8, 2146-2150); and Li et al. (Anal. Chem. 2008, 80, 9131-9134), the content of each of which is incorporated by reference herein in its entirety. Liquid samples loaded onto such a paper-based device can travel along the hydrophilic channels driven by capillary action.

Another application of the modified surface is to separate or concentrate compounds according to their different affinities with the surface and with the solution. Some compounds are preferably absorbed on the surface while other chemicals in the matrix prefer to stay within the aqueous phase. Through washing, sample matrix can be removed while compounds of interest remain on the surface. The compounds of interest can be removed from the surface at a later point in time by other high-affinity solvents. Repeating the process helps desalt and also concentrate the original sample.

In certain embodiments, chemicals are applied to the porous material to modify the chemical properties of the porous material. For example, chemicals can be applied that allow differential retention of sample components with different chemical properties. Additionally, chemicals can be applied that minimize salt and matrix effects. In other embodiments, acidic or basic compounds are added to the porous material to adjust the pH of the sample upon spotting. Adjusting the pH may be particularly useful for improved analysis of biological fluids, such as blood. Additionally, chemicals can be applied that allow for on-line chemical derivatization of selected analytes, for example to convert a non-polar compound to a salt for efficient electrospray ionization.

In certain embodiments, the chemical applied to modify the porous material is an internal standard. The internal standard can be incorporated into the material and released at known rates during solvent flow in order to provide an internal standard for quantitative analysis. In other embodiments, the porous material is modified with a chemical that allows for pre-separation and pre-concentration of analytes of interest prior to mass spectrum analysis.

Any solvents may be used that are compatible with mass spectrometry analysis. In particular embodiments, favorable solvents will be those that are also used for electrospray ionization. Exemplary solvents include combinations of water, methanol, acetonitrile, and THF. The organic content (proportion of methanol, acetonitrile, etc. to water), the pH, and volatile salt (e.g. ammonium acetate) may be varied depending on the sample to be analyzed. For example, basic molecules like the drug imatinib are extracted and ionized more efficiently at a lower pH. Molecules without an ionizable group but with a number of carbonyl groups, like sirolimus, ionize better with an ammonium salt in the solvent due to adduct formation.

Discontinuous Atmospheric Pressure Interface (DAPI)

In certain embodiments, a discontinuous atmospheric pressure interface (DAPI) is used with the bench-top or miniature mass spectrometer. Discontinuous atmospheric interfaces are described in Ouyang et al. (U.S. Pat. No. 8,304,718 and PCT application number PCT/US2008/065245), the content of each of which is incorporated by reference herein in its entirety.

Figure 15:
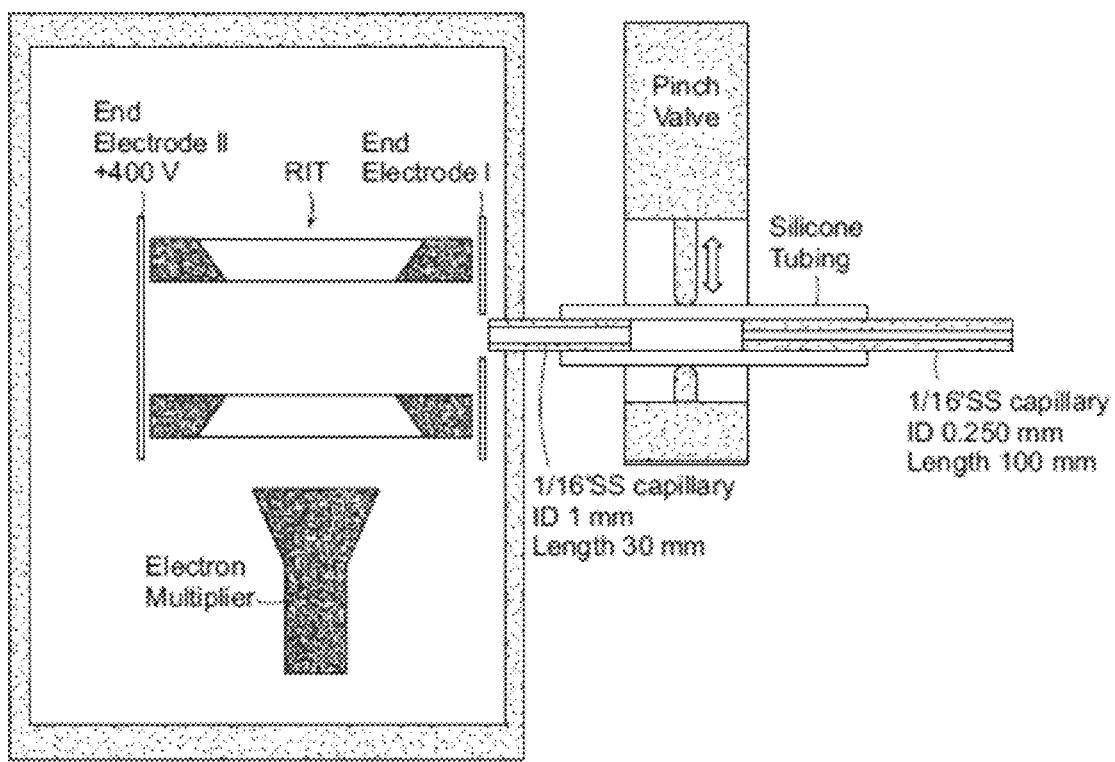
FIG. 15 shows a schematic showing a discontinuous atmospheric pressure interface coupled in a miniature mass spectrometer with rectilinear ion trap.

An exemplary DAPI is shown in FIG. 15. The concept of the DAPI is to open its channel during ion introduction and then close it for subsequent mass analysis during each scan. An ion transfer channel with a much bigger flow conductance can be allowed for a DAPI than for a traditional continuous API. The pressure inside the manifold temporarily increases significantly when the channel is opened for maximum ion introduction. All high voltages can be shut off and only low voltage RF is on for trapping of the ions during this period. After the ion introduction, the channel is closed and the pressure can decrease over a period of time to reach the optimal pressure for further ion manipulation or mass analysis when the high voltages can be is turned on and the RF can be scanned to high voltage for mass analysis.

A DAPI opens and shuts down the airflow in a controlled fashion. The pressure inside the vacuum manifold increases when the DAPI opens and decreases when it closes. The combination of a DAPI with a trapping device, which can be a mass analyzer or an intermediate stage storage device, allows maximum introduction of an ion package into a system with a given pumping capacity.

Much larger openings can be used for the pressure constraining components in the DAPI in the new discontinuous introduction mode. During the short period when the DAPI is opened, the ion trapping device is operated in the trapping mode with a low RF voltage to store the incoming ions; at the same time the high voltages on other components, such as conversion dynode or electron multiplier, are shut off to avoid damage to those device and electronics at the higher pressures. The DAPI can then be closed to allow the pressure inside the manifold to drop back to the optimum value for mass analysis, at which time the ions are mass analyzed in the trap or transferred to another mass analyzer within the vacuum system for mass analysis. This two-pressure mode of operation enabled by operation of the DAPI in a discontinuous fashion maximizes ion introduction as well as optimizing conditions for the mass analysis with a given pumping capacity.

The design goal is to have largest opening while keeping the optimum vacuum pressure for the mass analyzer, which is between $10^{-3}$ to $10^{-10}$ torr depending the type of mass analyzer. The larger the opening in an atmospheric pressure interface, the higher is the ion current delivered into the vacuum system and hence to the mass analyzer.

An exemplary embodiment of a DAPI is described herein. The DAPI includes a pinch valve that is used to open and shut off a pathway in a silicone tube connecting regions at atmospheric pressure and in vacuum. A normally-closed pinch valve (390NC24330, ASCO Valve Inc., Florham Park, N.J.) is used to control the opening of the vacuum manifold to atmospheric pressure region. Two stainless steel capillaries are connected to the piece of silicone plastic tubing, the open/closed status of which is controlled by the pinch valve. The stainless steel capillary connecting to the atmosphere is the flow restricting element, and has an ID of 250 µm, an OD of 1.6 mm (1/16") and a length of 10 cm. The stainless steel capillary on the vacuum side has an ID of 1.0 mm, an OD of 1.6 mm (1/16") and a length of 5.0 cm. The plastic tubing has an ID of 1/16", an OD of 1/8" and a length of 5.0 cm. Both stainless steel capillaries are grounded. The pumping system of the mini 10 consists of a two-stage diaphragm pump 1091-N84.0-8.99 (KNF Neuberger Inc., Trenton, N.J.) with pumping speed of 5 L/min (0.3 m3/hr) and a TPD011 hybrid turbomolecular pump (Pfeiffer Vacuum Inc., Nashua, N.H.) with a pumping speed of 11 L/s.

When the pinch valve is constantly energized and the plastic tubing is constantly open, the flow conductance is so high that the pressure in vacuum manifold is above 30 torr with the diaphragm pump operating. The ion transfer efficiency was measured to be 0.2%, which is comparable to a lab-scale mass spectrometer with a continuous API. However, under these conditions the TPD 011 turbomolecular pump cannot be turned on. When the pinch valve is deenergized, the plastic tubing is squeezed closed and the turbo pump can then be turned on to pump the manifold to its ultimate pressure in the range of $1 \times 10^5$ torr.

The sequence of operations for performing mass analysis using ion traps usually includes, but is not limited to, ion introduction, ion cooling and RF scanning. After the manifold pressure is pumped down initially, a scan function is implemented to switch between open and closed modes for ion introduction and mass analysis. During the ionization time, a 24 V DC is used to energize the pinch valve and the DAPI is open. The potential on the rectilinear ion trap (RIT) end electrode is also set to ground during this period. A minimum response time for the pinch valve is found to be 10 ms and an ionization time between 15 ms and 30 ms is used for the characterization of the discontinuous DAPI. A cooling time between 250 ms to 500 ms is implemented after the DAPI is closed to allow the pressure to decrease and the ions to cool down via collisions with background air molecules. The high voltage on the electron multiplier is then turned on and the RF voltage is scanned for mass analysis. During the operation of the DAPI, the pressure change in the manifold can be monitored using the micro pirani vacuum gauge (MKS 925C, MKS Instruments, Inc. Wilmington, Mass.) on Mini 10.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

The Examples herein show implementation of porous substrate spray ambient ionization using a bench-top and portable mass spectrometer for the detection of alkyl quaternary ammonium salts in a complex oil matrix. These salts are commonly used as active components in the formulation of corrosion inhibitors. The active components of the corrosion inhibitors were identified in oil and confirmed by their fragmentation patterns recorded using tandem mass spectrometry (MS/MS). The cations of alkyl and benzyl-substituted quaternary ammonium salts showed characteristic neutral losses of $C_nH_{2n}$ (n=carbon number of the longest chain) and $C_7H_8$, respectively. Individual quaternary ammonium compounds were detected at low concentrations (<1 ng/μL) and over a dynamic range of ~5 ppb-500 ppb. Direct detection of these compounds in complex oil samples without prior sample preparation or pre-concentration was also demonstrated using a miniature mass spectrometer at levels below 1 ng/μL.

Example 1

Chemicals, Reagents and Materials

Pure standard compounds with similar properties to the actives in quaternary ammonium corrosion inhibitors were purchased from Sigma-Aldrich (St. Louis, Mo.), namely, tetraoctylammonium bromide, tetradodecylammonium bromide, tetrahexylammonium bromide, tetrabutylammonium hexafluorophosphate, hexadecyltrimethylammonium bromide, benzylhexadecyldimethylammonium chloride, hexadecyltrimethylammonium bromide, and a mixture of alkyldimethylbenzyl ammonium chloride ($[C_6H_5CH_2N(CH_3)_2R]Cl$ where the alkyl group R is predominantly n-$C_{12}H_{25}$ but also contains m/z 332 ($C_{14}$) and m/z 360 ($C_{16}$) homologs). Samples were dissolved in methanol to make a stock solution at 1000 ppm. Working solutions were prepared by appropriate serial dilution with methanol/acetonitrile (1:1, v/v). Acetonitrile and methanol (both HPLC grade) were obtained from Mallinckrodt Baker Inc. (Phillipsburg, N.J.). An artificial mixture consisting of each of the model compounds at 100 ppb concentration was prepared so that approximately the same ion abundances were recorded. In order to mimic the oilfield conditions, vacuum pump oil (Inland 19 Petroleum Lubricating oil CAS Number: 64742-65-0) was used to dilute the stock solution of the model compounds to 10 ppb concentration and this sample was then analyzed without any pre-concentration or purification. Chromatography filter paper used for paper spray was purchased from Whatman (Whatman, no. 1, Whatman International Ltd., Maidstone, UK). Methanol/acetonitrile (1:1, v/v) was used as the spray solvent for all the paper spray experiment unless otherwise stated.

Example 2

Paper Spray Mass Spectrometry (PS-MS) Using a Bench-Top Mass Spectrometer

Experiments were first performed using a Thermo LTQ linear ion trap mass spectrometer (Thermo Scientific San Jose, Calif.) tuned for optimum detection of the precursor ion of interest. The instrument was set to record spectra in the automatic gain control mode for a maximum ion trap injection time of 100 ms; three microscans were combined per spectrum. The main experimental parameters used were as follows: paper spray solvent 10 μL of methanol/acetonitrile (1:1, v/v); voltage applied to the paper +3.5 kV in positive mode unless otherwise noted; capillary temperature, 150° C.; tube lens voltage +65 V; capillary voltage, +15 V. Tandem mass spectrometry experiments were performed using collision-induced dissociation (CID) in order to confirm the presence and identity of the analytes. These experiments were performed using an isolation window of 1.5 Thomson, (Th, i.e., m/z units) and 8-15% collision energy (manufacturer's unit) and the data recorded in the product ion scan mode (Schwartz et al., Anal. Chem., 1990, 62, 1809-1818).

Example 3

Paper Spray Mass Spectrometry Using a Miniature Mass Spectrometer

A paper spray ion source was interfaced, as shown in FIG. 1, to a miniature mass spectrometer the Mini 12.0 (Li et al., "Development and Performance Characterization of a Personal Mass Spectrometry System", 61st ASMS Conference on Mass Spectrometry and Allied Topics, Minneapolis, Minn., Jun. 9-13, 2013, MP 330). A miniature mass spectrometer is also described in PCT/US10/32881 and PCT/US2008/065245, the content of each of which is incorporated by reference herein in its entirety. The mass analysis system, the vacuum system, the control system and the detector are all integrated into a shoe-box sized aluminum box. The overall instrument uses 65 W average power and weighs 15 kg. The mass analyzer is a rectilinear ion trap (RIT; Sokol et al., Int. J. Mass Spectrom., 2011, 306, 187-195; and Xu et al., JALA, 2010, 15, 433-439) operating at a frequency of 1 MHz enclosed in a stainless steel manifold of 470 cm$^3$ volume (Gao et al., Anal. Chem., 2006, 78(17), 5994-6002). As a result of its simplified geometry and pressure tolerance, RITs have many advantages as a miniature mass analyzers as is evident in earlier applications (Sokol et al., Int. J. Mass Spectrom., 2011, 306, 187-195; Gao et al., Anal. Chem., 2006, 78(17), 5994-6002; and (March et al., Quadrupole Ion Trap Mass Spectrometry 2nd Edition, 2005, pp. 167-1'76). The capability for tandem mass spectrometry is especially valuable in enhancing the sensitivity and specificity of mixture analysis. The operating pressure range was in the range $1\times10^{-5}$ Torr to ca. $5\times10^{-2}$ Torr, with mass analysis scans being performed in the lower range of pressures.

Example 4

Interface to the Mini 12.0 Mass Spectrometer

To achieve an adequate vacuum, a discontinuous atmospheric pressure interface (DAPI; Ouyang, et al. Anal. Chem., 76, 4595-4605; Gao et al., Anal. Chem., 80, 7198-7205; Gao et al., Anal. Chem., 2008, 80, 4026-4032; and Gao et al., Int. J. Mass Spectrom., 2009, 283, 30-34) was used to directly introduce ions and the accompanying ambient air into the mass analyzer from the ambient environment. The pressure rises upon sample introduction and then falls again to levels suitable for mass analysis when the interface is closed. Unlike a conventional continuous ion introduction technique, DAPI admits discrete pulses of ion/air mixture to reduce the gas load on the pumps. In each sampling period, the DAPI is opened for 10-20 ms under the control of a pulse valve. During this period, ions are pulsed into the vacuum system for subsequent analysis. After the DAPI is closed, the neutral gas is pumped away so that the trapped ions can be mass analyzed. A DAPI can be coupled to a miniature mass spectrometer (Huang et al., Analyst, 2010, 135, 705-711; and Soparawalla et al., Analyst, 2011, 136, 4392-4396).

Example 5

Paper Spray Ionization for In Situ Analysis

The paper spray ion emitter was held in front of the Mini 12.0 mass spectrometer (Linfan et al., "Miniature Ambient Mass Analysis System", manuscript in preparation) as shown in FIG. 1, to achieve rapid in situ analysis of untreated (i.e., unmodified) complex mixtures. Results from the in situ experiment using a miniature mass spectrometer were compared with the results from a typical bench-top commercial instrument operating in a typical lab setting.

Example 6

Tandem Mass Spectrometry

Mass-selected ions were fragmented through energetic collisions with neutral gas molecules using collision-induced dissociation (CID) in the Mini 12.0 instrument. After the ions had been introduced by opening the DAPI valve for 15 ms, an 850 ms cooling time was provided to restore the vacuum before ion isolation. A broadband stored waveform inverse Fourier transform (SWIFT) signal from 10 kHz to 500 kHz with a notch between 97 kHz and 105 kHz was applied to the x electrodes of the RIT at an amplitude of 3.5 $V_{p-p}$ for 175 ms to isolate the precursor ions of interest (the study was done at a Mathieu parameter $q_z$ value of 0.185 for each ion of interest and the RF amplitude was appropriately set to place each ion at this value) (Guan et al., Int. J. Mass Spectrom. Ion Process, 1996, 157-158, 5-37). To perform CID, an AC signal of 0.45 V at a frequency of 102 kHz was then applied to the x electrodes of the RIT for 40 ms after the isolation step (Sokol et al., Int. J. Mass Spectrom., 2011, 306, 187-195). The AC excitation signal was ramped from 1.3 $V_{p-p}$ to 6.6 $V_{p-p}$ at 1000 mMHz for resonance ejection while the RF amplitude was ramped from 1 $kV_{p-p}$ to 5 $kV_{p-p}$ at 1 MHz in the acquisition time segment.

Example 7

Semi-Quantitative Analysis

The lower detection of limit (LOD) was determined as the concentration that produces a signal higher than 3 times of standard deviation plus the mean value of the blank, in the MS/MS mode. Using a commercial linear ion trap mass spectrometer, the detection limits of four model compounds in both neat solution and oil matrix were determined to be in the low ppb level. Using the miniature ion trap (Mini 12), detection limits were ca. 10-50 times higher than those obtained using the commercial instrument, as summarized in Table 1.

Figure 2:
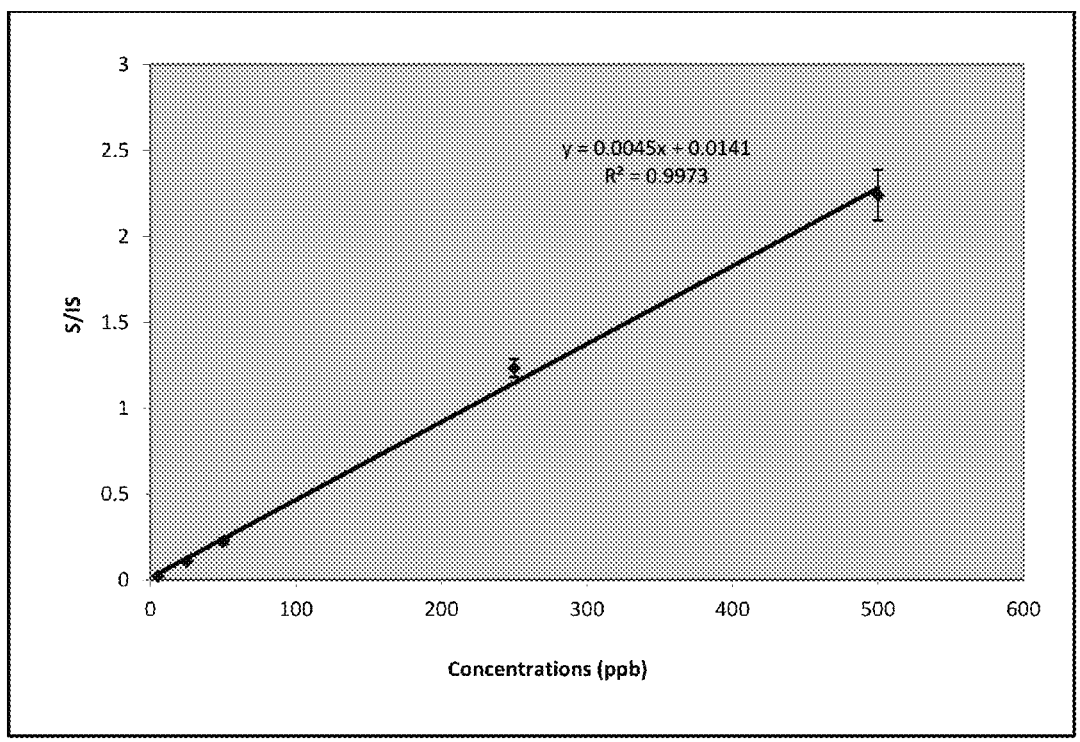
FIG. 2 is a calibration curve for the quantitative analysis of ammonium salts in oil matrix using a commercial ion trap mass spectrometer

Quantitative analysis of the salt tetraoctylammonium bromide in oil was achieved by calibration using another ammonium salt (tetraheptylammonium bromide, 250 ppb) as internal standard. The signal intensity ratios of the most abundant MS/MS transitions were found to be linear in the range from 5 ppb to 500 ppb. (y=0.0045x+0.00141, $R^2$=0.9973), as shown in FIG. 2. The measurements within this range had a relative standard deviation of <10% when three replicates were taken.

TABLE 1

Detection limits (LOD) of the analyzed quaternary ammonium model compounds in pg absolute

| | LOD using commercial ion trap (pg) | | LOD using mini ion trap (pg) | |
| --- | --- | --- | --- | --- |
| Compound | neat solvent | Oil matrix | neat solvent | Oil matrix |
| Tetraoctylammonium bromide | 0.9 | 1.1 | 81 | 184 |
| Tetrahexylammonium bromide | 0.6 | 9.5 | not available | not available |
| Tetrabutylamonium hexafluorophosphate | 0.9 | 11.6 | not available | not available |
| Benzylhexadecyldimethyl ammonium chloride | 10.2 | 27.6 | 282 | 472 |

Example 8

Quaternary Ammonium Salt Analysis Using Bench-Top Ion Trap Mass Spectrometer

Figure 3A:
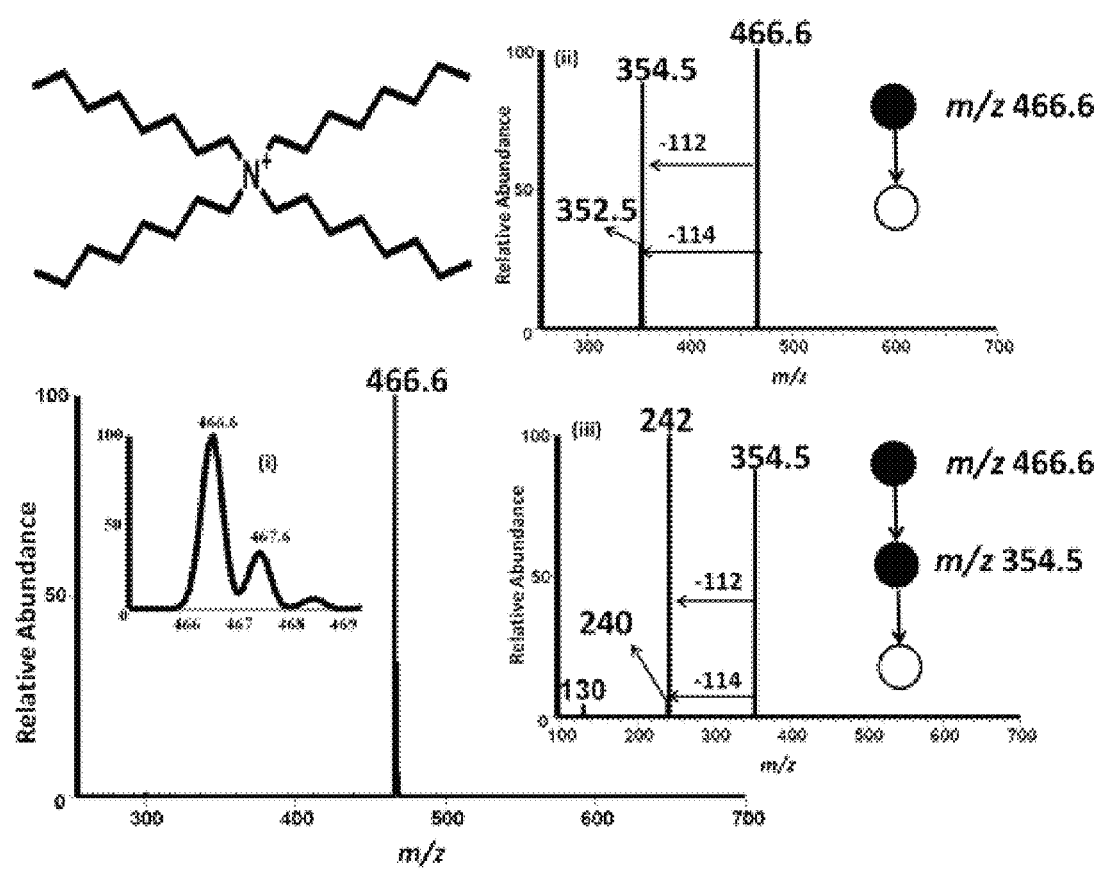
FIGS. 3A-B are mass spectra showing positive ion mode paper spray mass spectra for quaternary ammonium corrosion inhibitor model compounds analyzed using a bench-top ion trap instrument. Absolute amounts of analytes spotted onto filter paper and ionized in air by application of an electric potential were 100 pg of each compound in 1 uL of oil, viz. 100 ppb.

Two different groups of nitrogenous corrosion inhibitors (both quaternary ammonium salts) were studied by paper spray mass spectrometry. We first optimized paper spray ionization conditions using a bench-top ion trap mass spectrometer to record positive ion data for the quaternary ammonium corrosion inhibitor compounds. This was performed by applying 0.1 ng/µL (1 µL of 100 ppb solution) of the corrosion inhibitor solution in vacuum pump oil, to a paper triangle, then adding acetonitrile/methanol solvent and recording data using the Thermo LTQ. These mass spectra showed intact cations with little or no fragmentation or interference from the oil matrix (FIG. 2). The remarkable absence of signal due to the oil components is consistent with the high ionization efficiency of pre-charged organic salts, a well-known feature of many different types of ionization methods. Characterization of the individual intact cations was achieved by tandem mass spectrometry; for example, insert (ii) of FIG. 3A shows that CID of the intact tetraoctylammonium cation at m/z 466.6 gives two fragment ions (a major product at m/z 354.5 and minor product 352.5, with loss of neutral octene (MW 112) and octane (MW 114), respectively (Sigsby et al., Organic Mass Spectrom., 1979, 14, 557). The stability and abundance of the product ions allowed three-stage mass spectrometry (MS/MS/MS) experiments to be performed. In this particular case, CID of the product ion at m/z 345.5 yielded further fragment ions at m/z 242 (major) and m/z 240 (minor) through sequential losses of octene (presumably 1-octene, $CH_3$—$(CH_2)_5$—$CH$=$CH_2$, MW 112) and octane (presumably n-octane, $CH_3$—$(CH_2)_5$—$CH$—$CH_2$, MW 114). Such multiple-stage MS experiments allow definitive confirmation of the identity of the analyte (Jackson et al., Eur. Mass Spectrom., 1997, 3, 113-120; Jackson et al., Int. J. Mass Spectrom., 2004, 238, 265-277; Jackson et al., Rapid Commun. Mass Spectrom., 2006, 20, 2717-2727; and Busch et al., Mass Spectrometry/Mass Spectrometry: Techniques and applications of Tandem Mass Spectrometry, VCH Publishers Inc., New York, 1988.)

Figure 3B:
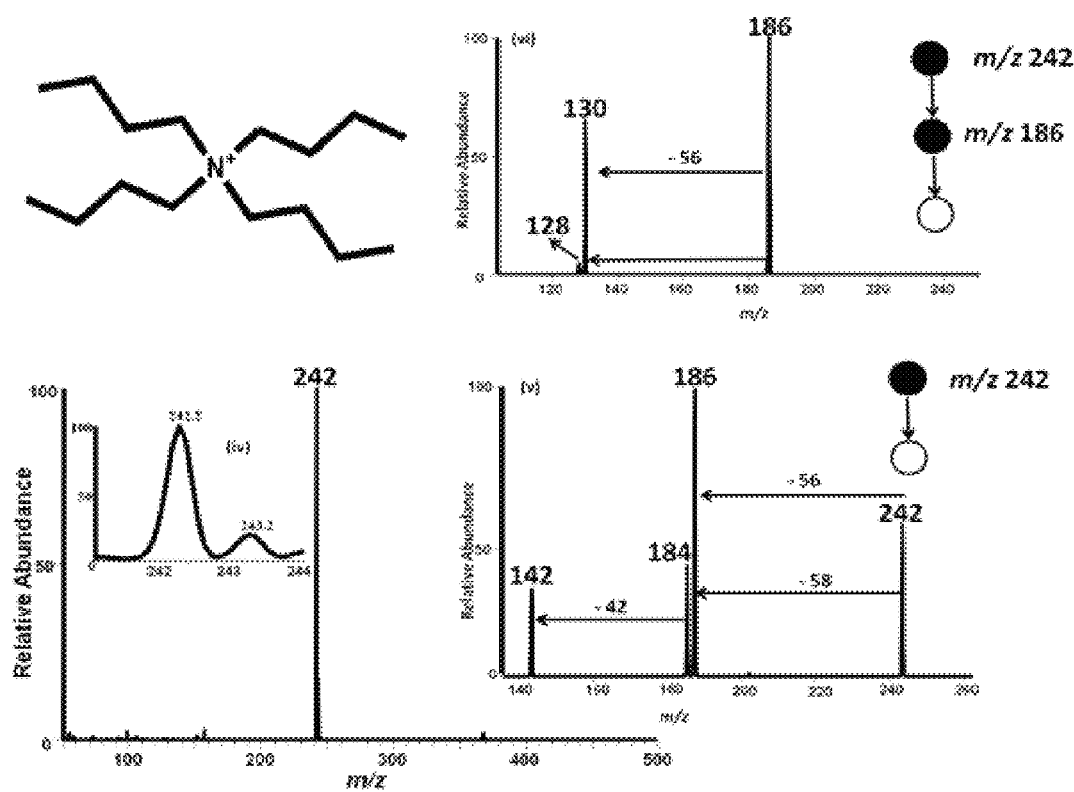

Similarly, other model compounds including hexadecyltrimethylammonium bromide, tetradodecylammonium bromide, tetrahexylammonium bromide, and benzylhexadecyldimethylammonium chloride were analyzed by paper spray MS using the Thermo LTQ commercial instrument, see FIGS. 7-10. The nitrogenous corrosion inhibitors are available with different counterions, a property that influences the inhibition performance of the salts (Treybig, U.S. Pat. No. 4,957,640). As demonstrated by the analysis of tetrabutylammonium hexafluorophosphate (FIG. 3B), the positive ion paper spray-MS method is insensitive to the type of anion associated with the quaternary ammonium cation. It was also found that both short and long chain cations can be analyzed effectively. Table 2 provides a summary of data for all the model compounds studied, including their CID fragmentation patterns. Just as in the case of the tetraoctylammonium cation (FIG. 3A), the elimination of both neutral alkene ($C_{11}H_{2n}$) and alkane ($C_{11}H_{2n+2}$) was observed during CID for all alkyl quaternary ammonium cations studied (Scheme 1 A and B). It is important to note that the fragmentation pattern was also observed for the long and short chain model compounds. For example, $MS^2$ and $MS^3$ spectra for the short chain tetrabutylammonium cations at m/z 242 and m/z 186 via successive eliminations of butene (MW 56) and butane (MW 58) are evident in FIG. 3B insert (v)-(vi).

TABLE 2

Structures and CID product ions of quaternary ammonium compounds analyzed in oil

| Name | Structure | MW (cation) | $MS^2$ Transitions | $MS^3$ Transitions |
|---|---|---|---|---|
| Tetraoctyl-ammonium bromide | 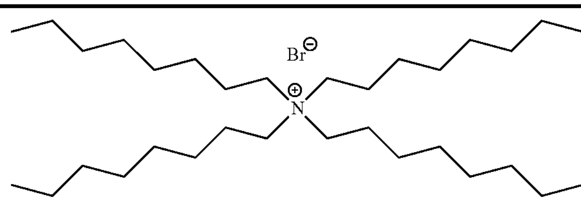 | 466.6 | 466.6→354.5 (loss of $C_8H_{16}$) 466.6→352.5 (loss of $C_8H_{18}$) | 466.6→354.5→242 (Loss of $C_8H_{16}$) 466.6→352.5→240 (Loss of $C_8H_{18}$) |
| Tetra-dodecyl-ammonium bromide | 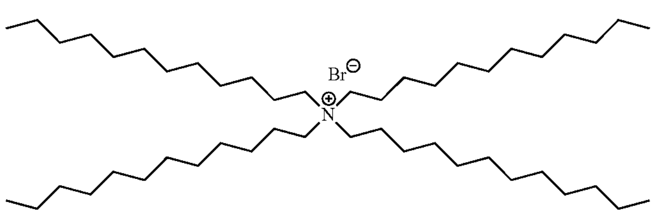 [SMILES: CCCCCCCCCCCC[N+](CCCCCCCCCCCC)(CCCCCCCCCCCC)CCCCCCCCCCCC ; [Br-]] | 691.0 | 691→522 (Loss of $C_{12}H_{24}$) 691→520 (Loss of $C_{12}H_{26}$) | 691→522→354.5 (Loss of $C_{12}H_{24}$) 691→520→352.5 (Loss of $C_{12}H_{26}$) |
| Tetrahexyl-ammonium bromide | 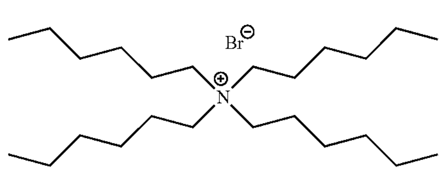 [SMILES: CCCCCC[N+](CCCCCC)(CCCCCC)CCCCCC ; [Br-]] | 354.7 | 354.7→270 (loss of $C_6H_{12}$) 354.7→268 (loss of $C_6H_{14}$) | 354.7→270→186 ($C_6H_{12}$) 354.7→268→184 ($C_6H_{24}$) |
| Tetrabutyl-ammonium hexafluoro-phosphate | 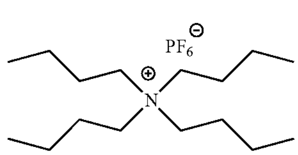 [SMILES: CCCC[N+](CCCC)(CCCC)CCCC ; "PF6"] | 242.0 | 242→186 (loss of $C_4H_8$) 242→184 (loss of $C_4H_{10}$) | 242→186→130 (loss of $C_4H_8$) 242→186→128 (loss of $C_4H_{10}$) |

TABLE 2-continued

Structures and CID product ions of quaternary ammonium compounds analyzed in oil

| Name | Structure | MW (cation) | MS² Transitions | MS³ Transitions |
|---|---|---|---|---|
| Hexadecyl-Trimethyl-ammonium bromide | 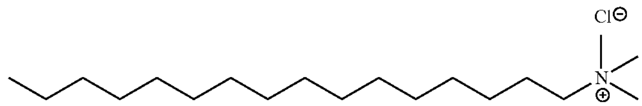 [SMILES: [Cl-] ; CCCCCCCCCCCCCCCC[N+](C)(C)C] | 284.0 | Below Scan range | Below scan range |
| Benzyl-hexadecyl-dimethyl-ammonium chloride | 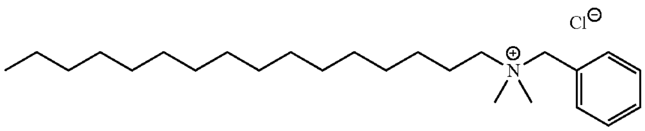 [SMILES: [Cl-] ; CCCCCCCCCCCCCCCC[N+](C)(C)Cc1ccccc1] | 360.0 | 360→168 (loss of $C_7H_8$) | Below scan range |

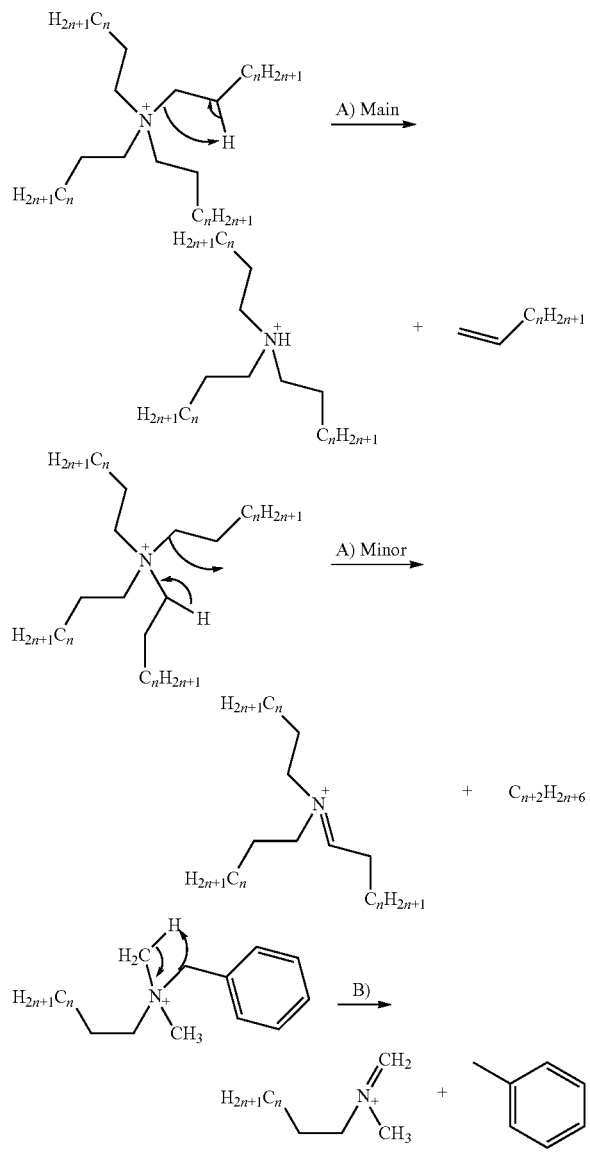

Scheme 1 Suggested fragmentation pathway for the A) alkyl and B) benzyl-substituted ammonium salts model compounds based on CID data.

Figure 4A:
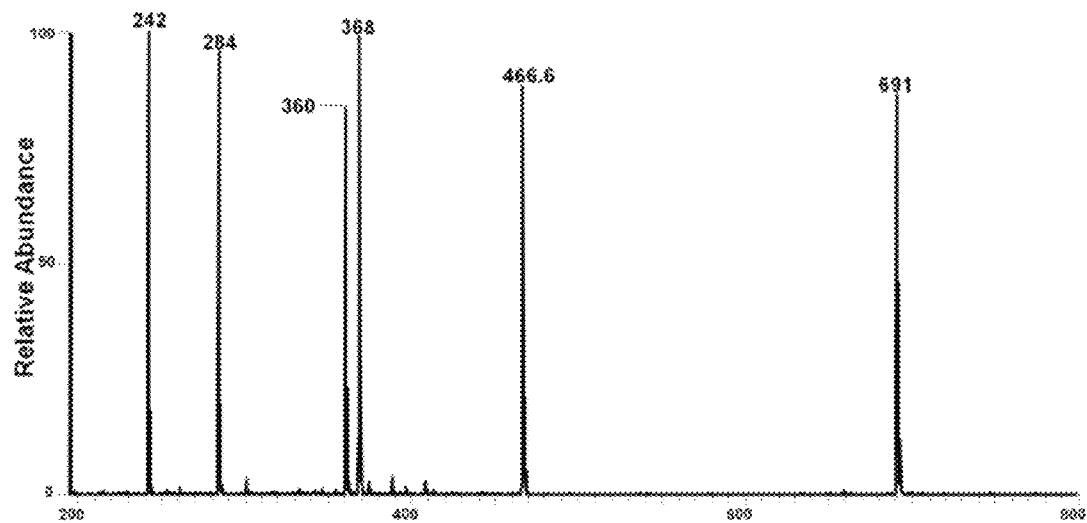
FIG. 4A is a positive ion mode paper spray mass spectrum for the model compounds in mixtures in vacuum pump oil analyzed using a benchtop instrument; tetrabutylammonium bromide gives the intact cation at m/z 242, hexadecytrimethylammonium bromide at m/z 284, benzylhexadecyldimethylammonium chloride at m/z 360, tetraoctylammonium bromide at m/z 466.6 and tetradodecylammonium bromide at m/z 691.
Figure 4B:
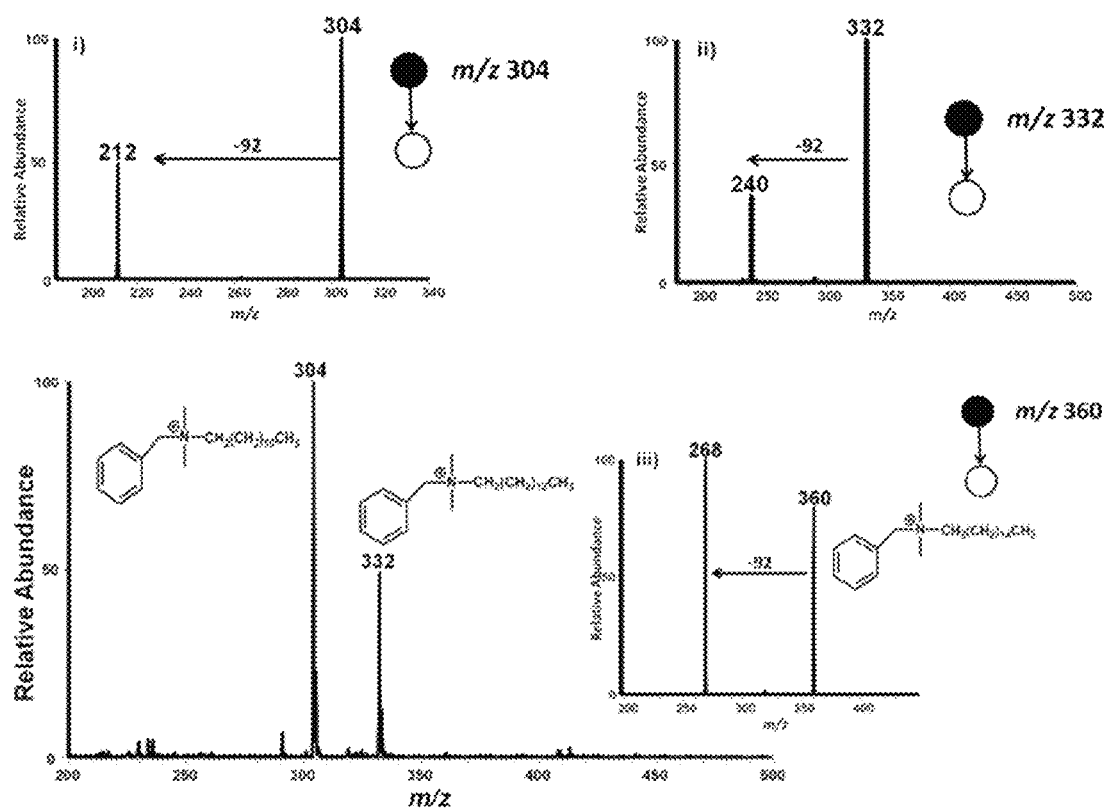
FIG. 4B is a typical positive ion paper spray mass spectra for alkyldimethylbenzyl ammonium chloride $[C_6H_5CH_2N (CH_3)_2R]Cl$ in which R is predominantly n-$C_{12}H_{25}$ but also contains $C_{14}$ and $C_{16}$ homologs) standard analyzed using a benchtop ion trap mass spectrometer. Inserts i), ii) and iii) are the CID mass spectra for the m/z 304 ($C_{12}$), m/z 332 ($C_{14}$), m/z 360 ($C_{16}$) respectively.
Figure 11:
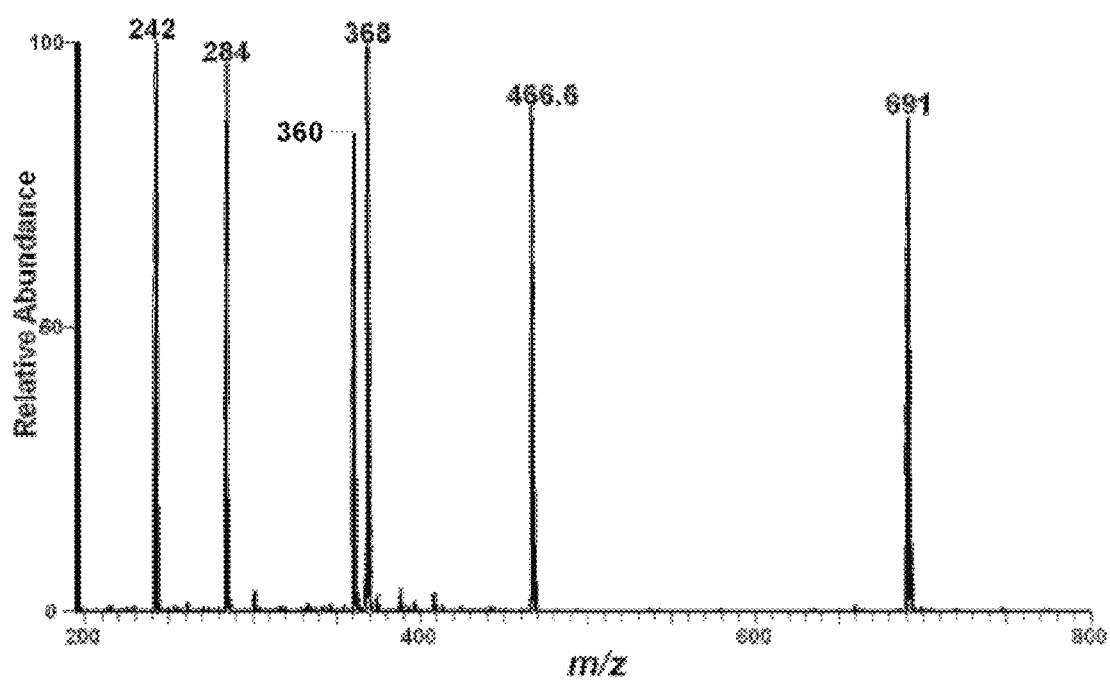
FIG. 11 is a positive ion mode paper spray mass spectrum for artificial mixtures of model compounds analyzed using a benchtop instrument. Tetrabutylammonium bromide was observed at m/z 242.0, hexadecytrimethylammonium bromide at m/z 284.0, benzylhexadecyldimethylammonium chloride at m/z 360.0, tetraoctylammonium bromide at m/z 466.6 and tetradodecylammonium bromide at m/z 691.0.
Figure 12:
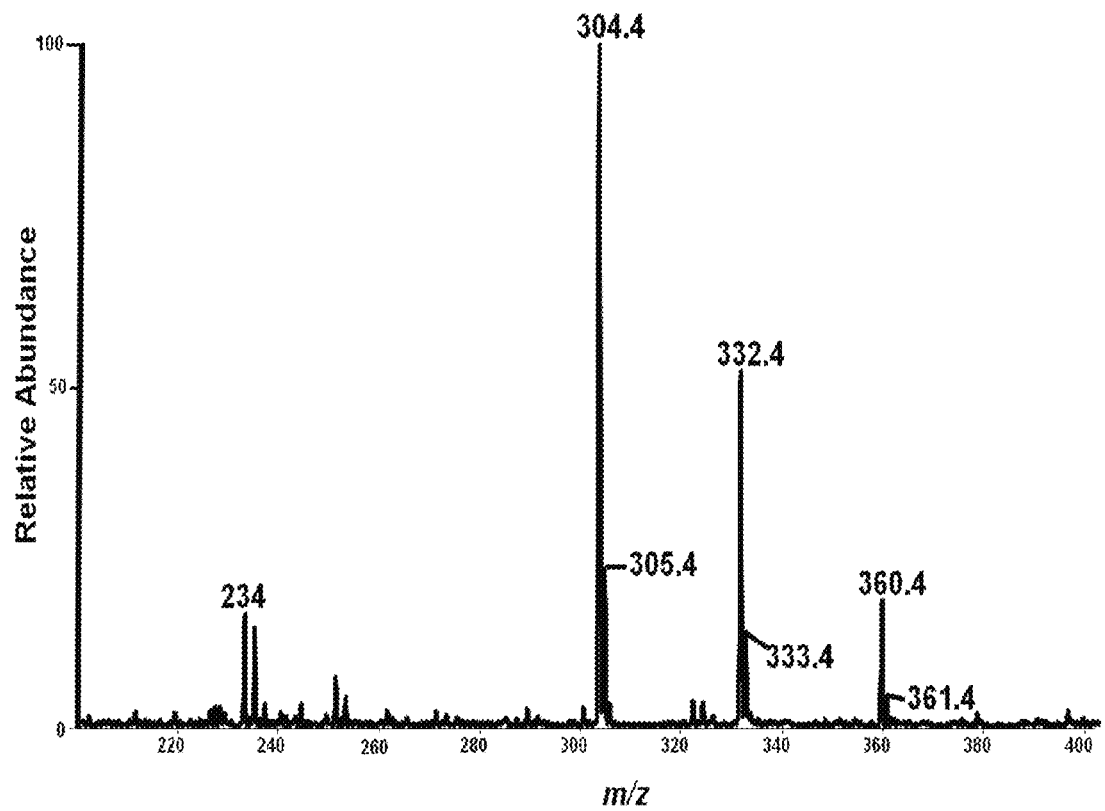
FIG. 12 is a typical positive ion paper spray mass spectra for a mixture of alkyl dimethylbenzyl ammonium chloride salts $[C_6H_5CH_2N(CH_3)_2R]Cl$ where R is predominantly n-$C_{12}H_{25}$ (also contains small amounts of m/z 332 ($C_{14}$) and m/z 360 ($C_{16}$) homologs) standard analyzed using a benchtop ion trap mass spectrometer. The trace levels of $C_{16}$ homolog, are manifest in the relative abundances compared with other components in the mixture.
Figure 13:
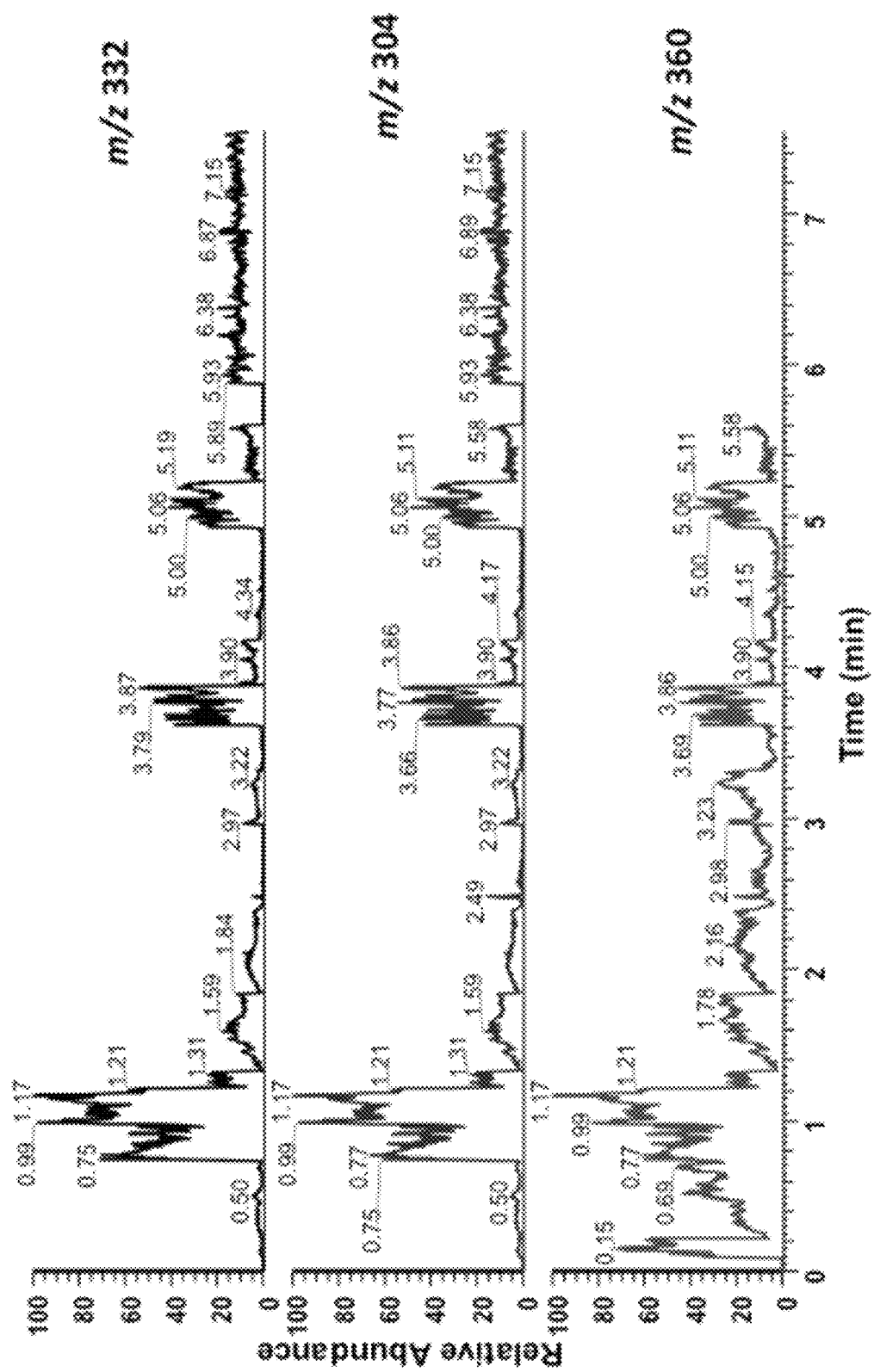
FIG. 13 shows ion chronograms for the for alkyl dimethylbenzyl ammonium chloride $[C_6H_5CH_2N (CH_3)_2R]Cl$ where R is predominantly n-$C_{12}H_{25}$; data for the homologs $C_{14}$ (m/z) 332, $C_{12}$ (m/z) 304, and $C_{16}$ (m/z) 360 are shown.

Ionization using paper spray-MS was also used to analyze quaternary ammonium corrosion inhibitors in mixtures. Firstly, an artificial mixture was prepared using equal volumes of the quaternary ammonium corrosion compounds in acetonitrile/methanol (1:1, v/v) to form a mixture of active corrosion inhibitor components. The mixture was then analyzed by paper spray-MS under the same conditions as described above: i.e., 10 pg of each compound (in 1 μL of oil) of corrosion inhibitor solution was spiked onto a paper triangle and analyzed using the commercial ion trap mass spectrometer, as shown in with a typical mass spectrum being shown in FIG. 11. Next a second mixture including alkyldimethylbenzyl ammonium chloride salts was prepared by mixing equal amounts of the model compounds in pump oil. Analysis of this mixture by paper spray-MS was again achieved without any sample pretreatment, and the resulting mass spectrum is shown in FIGS. 4A-B. Both mixtures gave relatively stable paper spray signals and produced no observable ion fragmentation in the full scan mass spectrum. Relative signal intensities from these mixtures in pump oil corresponded to the amounts in the analyte mixture. Changing the spray solvent from methanol to methanol/acetonitrile showed no effect on the ion signal intensity of signal to noise ratio as described in FIG. 12. Note that this standard sample (alkyldimethylbenzyl ammonium chloride) contains only trace amounts of $C_{16}$ and this is evident from the relative abundance of this mass spectral signal from this ion compared with that of other components in the mixture (FIG. 12) and in the corresponding total ion chronograms (TIC). In the latter experiment, no m/z 360 ($C_{16}$) ion signal is observed at 5.5 min, see FIG. 13.

Example 9

Corrosion Inhibitor Analysis Using Portable Ion Trap Mass Spectrometer

Figure 5A:
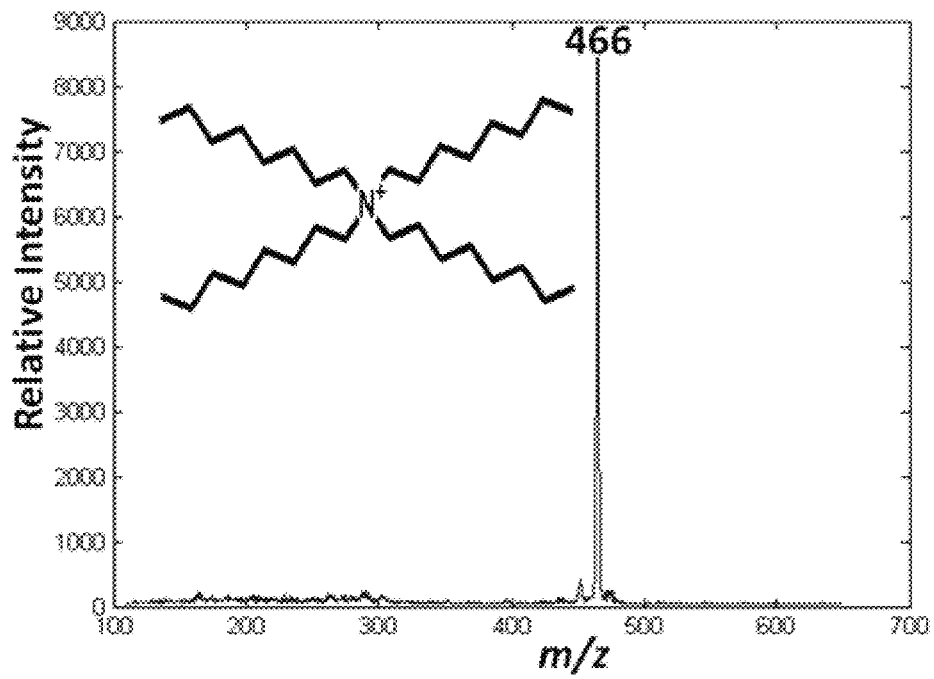
FIGS. 5A-D are positive ion paper spray mass spectra of quaternary ammonium corrosion inhibitor model compounds analyzed in oil (1 µL) using a handheld miniature instrument. Absolute amounts of analytes spotted on paper were 100 pg of each compound.
Figure 5B:
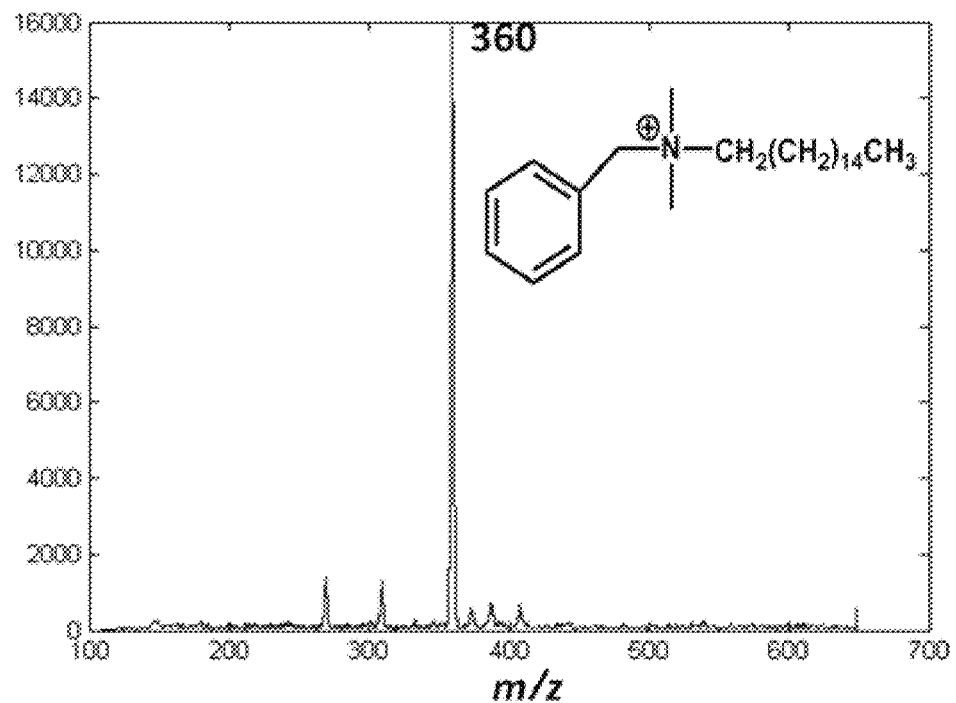
Figure 5C:
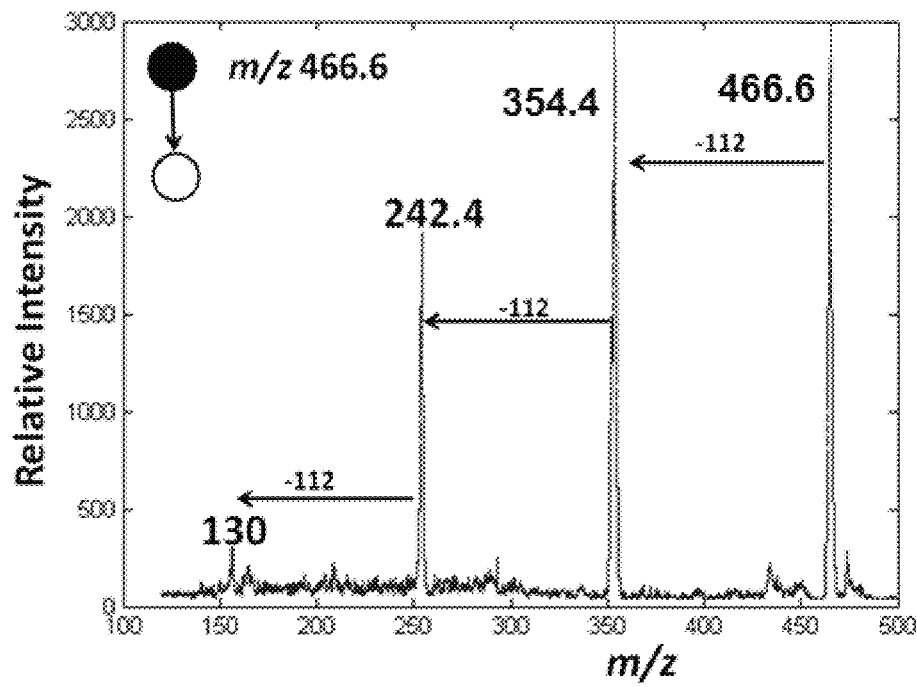
Figure 5D:
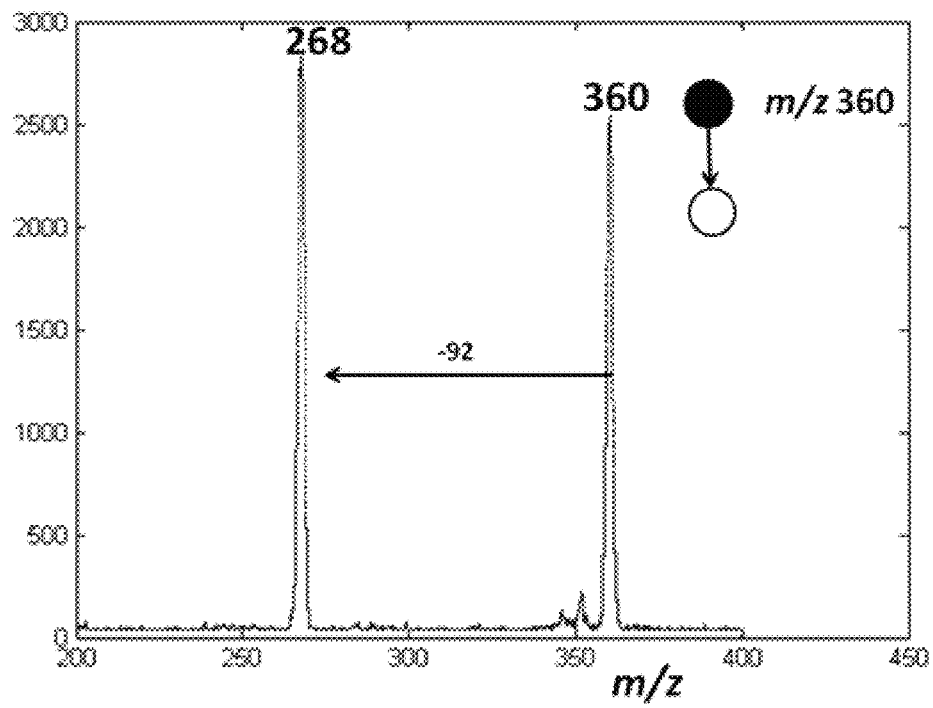

The success of paper spray-MS in the analysis of quaternary ammonium salts from an oil matrix using the bench-top instrument led to analyzing crude oil with a miniature ion trap instrument (Mini 12.0). Mixtures as well the individual alkyl and benzyl quaternary ammonium salts were analyzed using the Mini 12.0 with paper spray ionization. FIGS. 5A-B show data for 1 ng/μL for tetraoctylammonium bromide and benzylhexadecyldimethylammonium chloride, applied to the paper in 1 μL of pump oil. As was observed, paper spray-MS using the Mini 12.0 gave a high ion signal-to-noise ratio even at this low level of analyte. Both the LTQ and the Mini signals were high enough to allow the identity of these compounds to be easily confirmed by tandem MS. Even though the Mini 12.0 operates at a relatively high pressure compared with the commercial instrument, little fragmentation was observed in the full scan mass spectra. The structural information however, is readily available from MS/MS (FIGS. 5C-D). Again, the tetraoctylammonium cation, m/z 466, fragments on the Mini 12.0 instrument through sequential loss of octene (MW 112) to give ions at m/z 354, 244 and 130. By contrast with the tetraalkyl salts, the most stable neutral species eliminated from the intact cation, m/z 360, of the trialkylaryl salt, benzylhexadecyldimethylammonium during CID WAS toluene (MW 92) and not an alkene derived from the alkyl groups attached to the quaternary nitrogen. This fragmentation pathway yields a product ion at m/z 268 (FIG. 5D). Such a simple fragmentation allowed easy quantification of various aryltrialkyl salts having different alkyl chain lengths in pump oil (Table 3).

TABLE 3

Structures and Product Ions of CID of the Salt $[C_6H_5CH_2N(CH_3)_2R]^+Cl^-$ Analyzed in Pump Oil by PS-MS using Benchtop and Miniature Instruments

| Active corrosion compound | MW (Cation) | MS/MS Transitions | Ion Loss |
|---|---|---|---|
| Quat $C_{12}$ | 304 | m/z 304 → 212 | 92 |
| Quat $C_{14}$ | 332 | m/z 332 → 240 | 92 |
| Quat $C_{16}$ | 360 | m/z 360 → 268 | 92 |

Figure 6A:
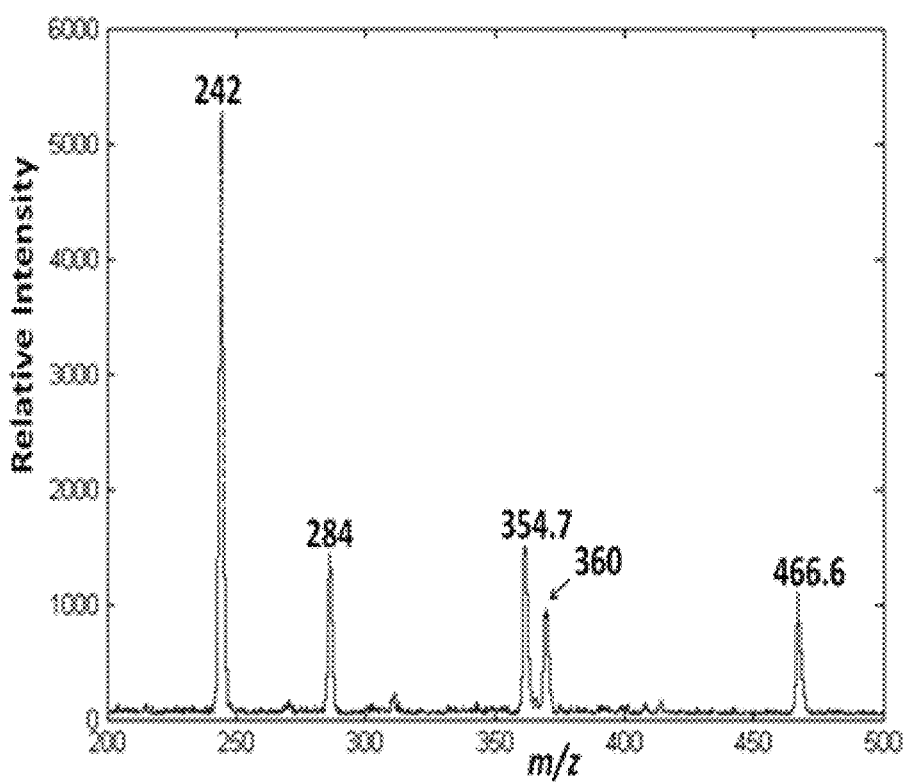
FIG. 6A is a positive ion paper spray mass spectrum for the model compounds artificial mixtures in vacuum pump oil analyzed using a handheld miniature instrument absolute amounts of analytes was spotted on paper were 1 ng/µL (absolute concentration); tetrabutylammonium bromide at m/z 242, hexadecytrimethylammonium bromide at m/z 284, benzylhexadecyldimethylammonium chloride at m/z 360, tetraoctylammonium bromide at m/z 466.6 and tetradodecylammonium bromide at m/z 691.
Figure 6B:
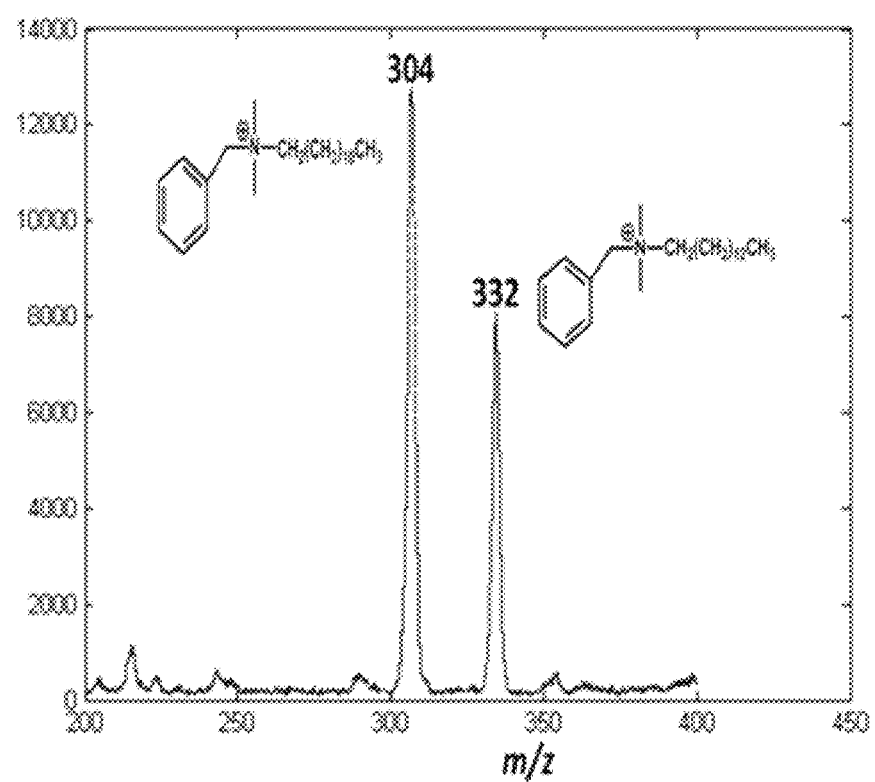
FIG. 6B is a typical positive ion paper spray mass spectra for alkyldimethylbenzyl ammonium chloride $[C_6H_5CH_2N (CH_3)_2R]Cl$ where R is predominantly n-$C_{12}H_{25}$ but also contains m/z 332 ($C_{14}$) and m/z 360 ($C_{16}$) homologs) standard analyzed using a benchtop ion trap mass spectrometer.
Figure 6C:
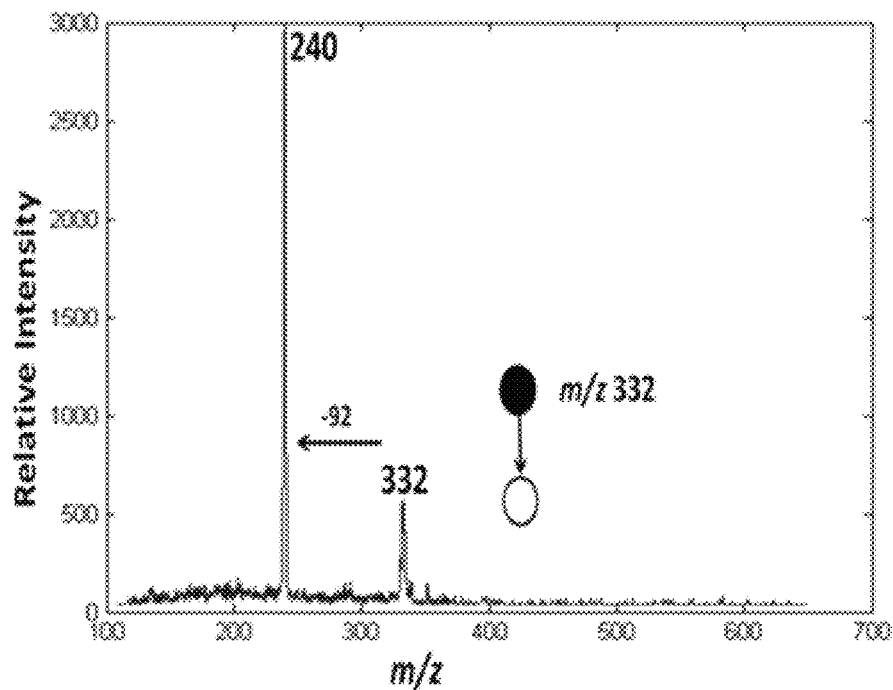
FIGS. 6C-D show the CID MS/MS data for the of m/z 304 ($C_{12}$) and m/z 332 ($C_{14}$) mixture components, respectively.
Figure 6D:
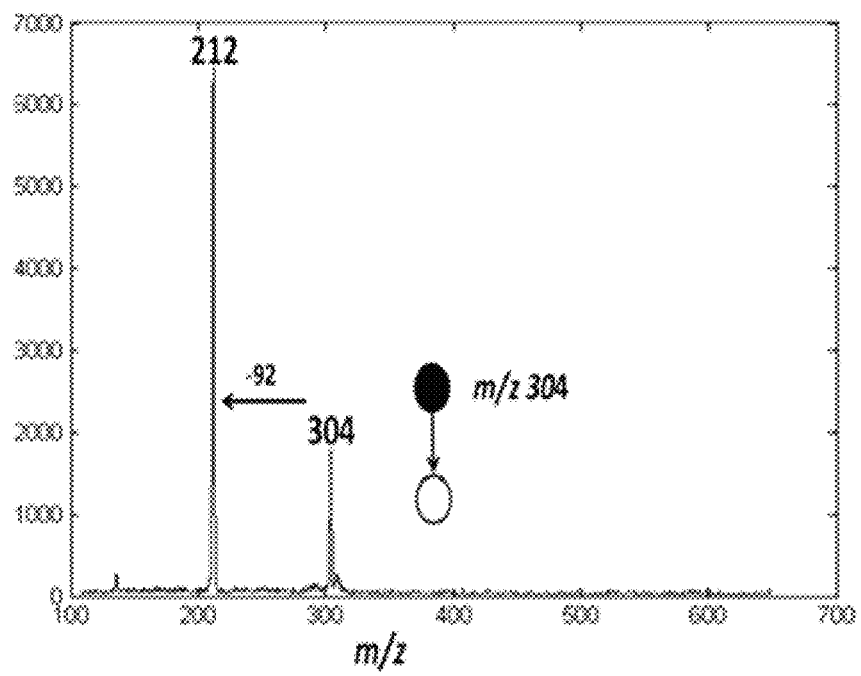
Figure 7:
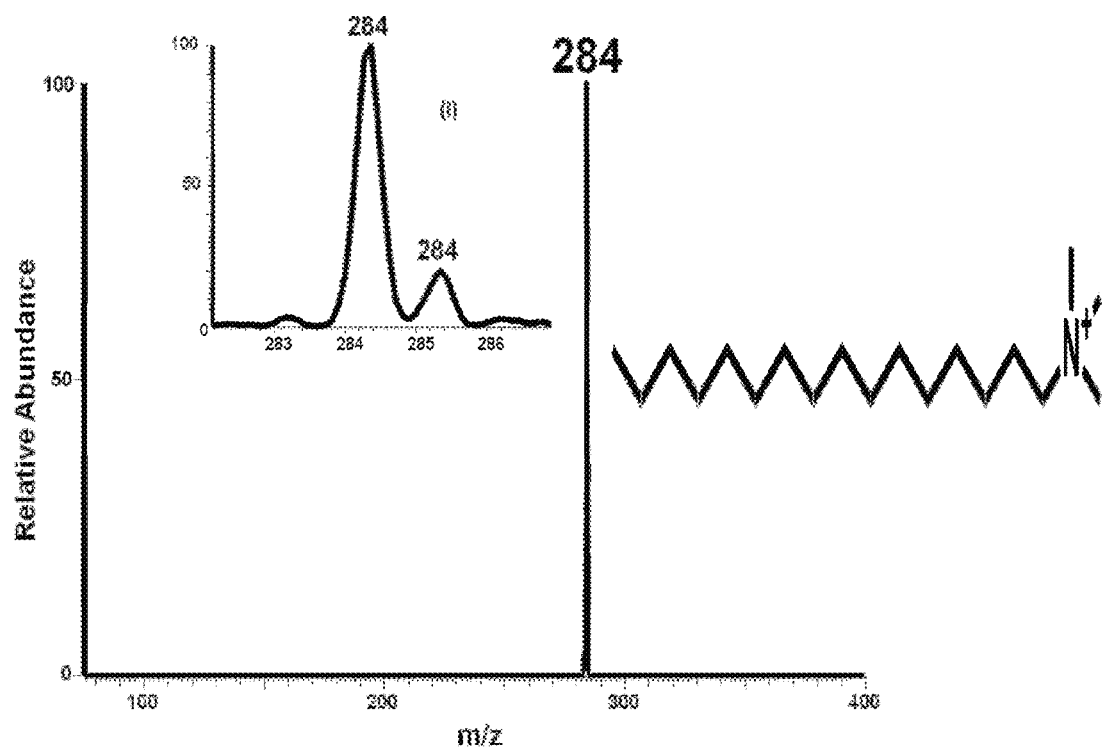
FIG. 7 is a positive paper spray-MS mass spectrum of hexadecyltrimethylammonium bromide. Insert (i) shows the isotopic distribution of the analyte, tandem mass spectrometry (MS/MS) of the hexadecyltrimethylammonium cation at m/z 284.0 did not return good signal since the expected major fragment is below the low mass cut off the instrument.
Figure 8:
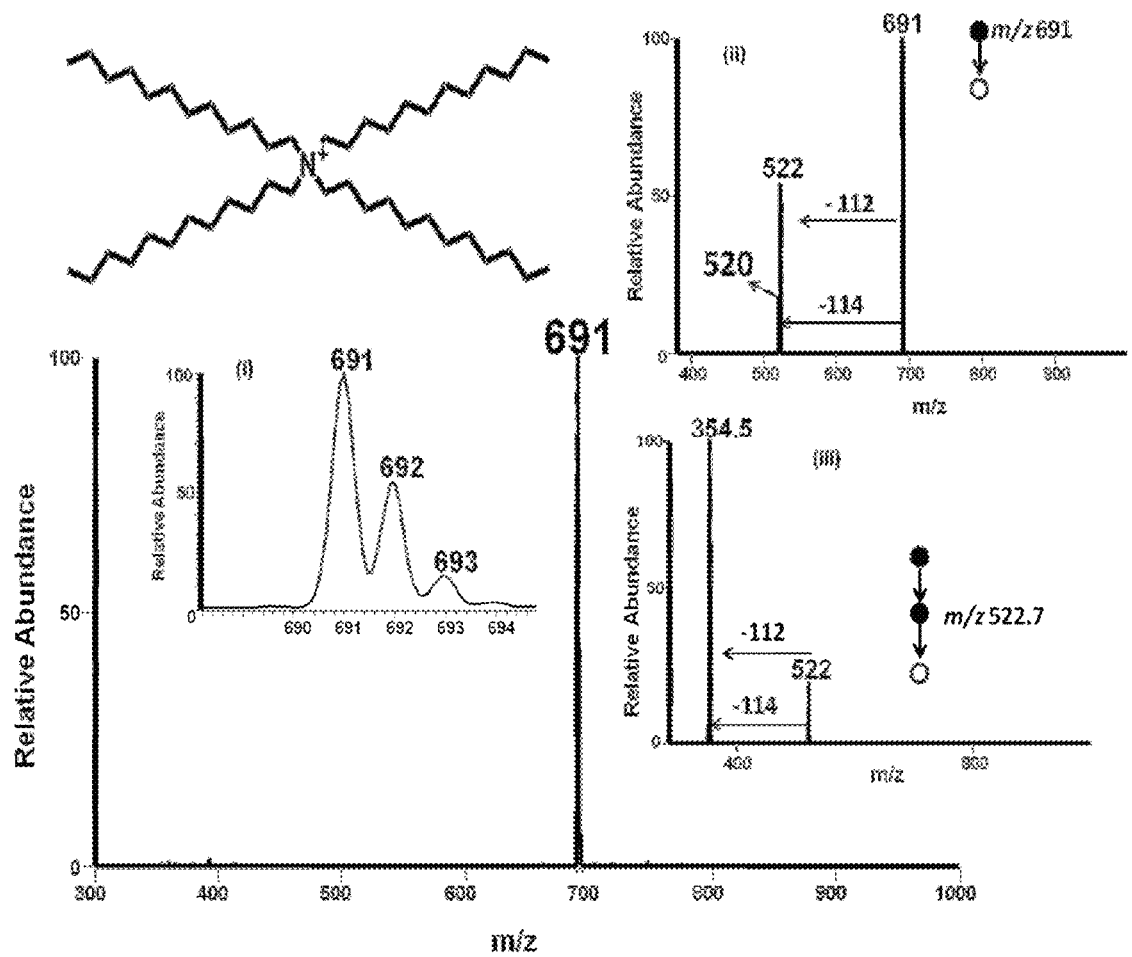
FIG. 8 is a positive paper spray-MS mass spectrum of tetradodecylammonium bromide. Insert (i) shows the isotopic distribution of the analyte, (ii)-(iii) Tandem mass spectrometry (MS/MS) of the tetraoctylammonioum cation at m/z 691.0 gives a major fragment ion at m/z 522.0 with a alkene loss of 112.0 and a minor fragment ion at 520.0 with a alkane loss of 114, which confirm the structure. Again (iii) MS/MS/MS of the major fragment ion at m/z 522.0 (major) fragments further to give an ion at m/z 354.5 and ion at m/z 352.5 with a neutral loss of –[112] and –[114] respectively further confirming the identity of the compound.
Figure 9:
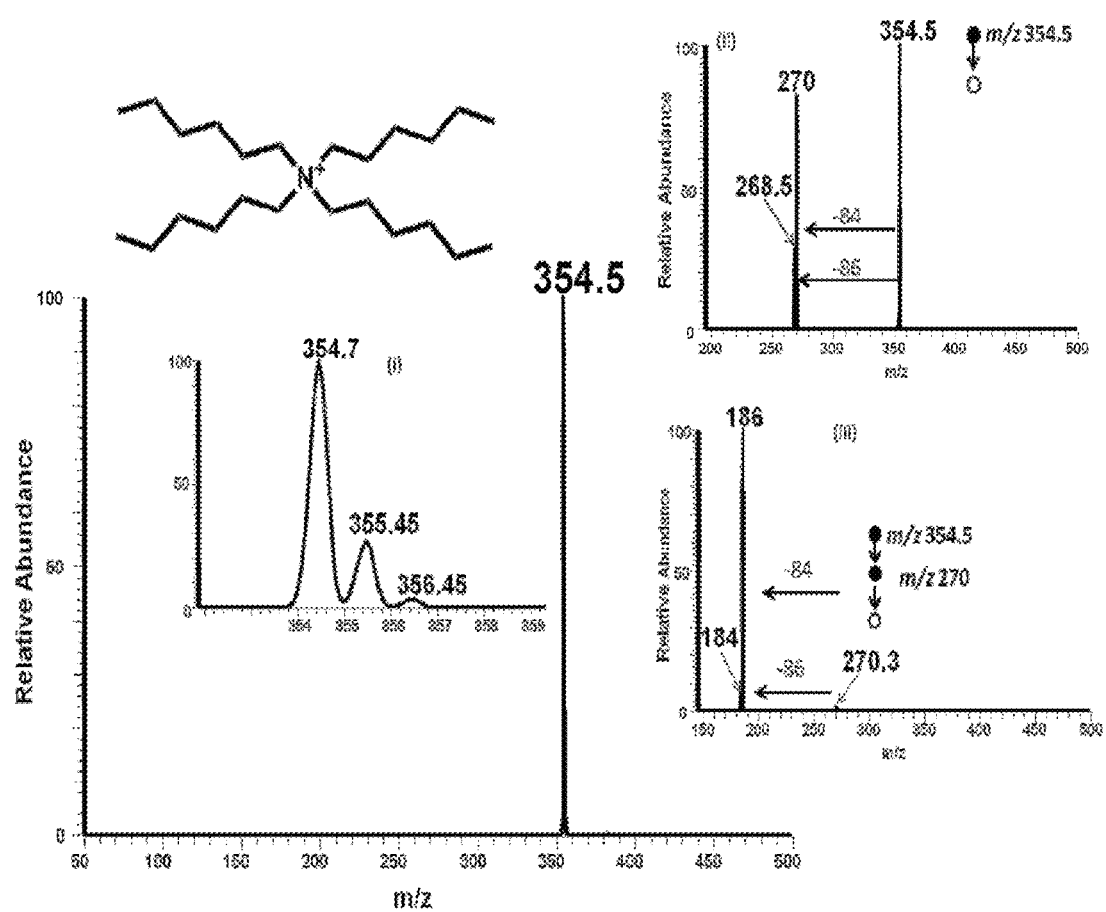
FIG. 9 is a positive paper spray-MS mass spectrum of tetrahexylammonium bromide. Insert (i) shows the isotopic distribution of the analyte ion, (ii)-(iii) Tandem mass spectrometry (MS/MS) of the tetrahexylammonium cation at m/z 354.7 gives a major fragment ion at m/z 270.0 with a loss of alkene –[84] and a minor fragment ion at 268.5 with a loss of alkane –[86] that confirms the structure. Again (iii) MS/MS/MS of the major fragment ion at m/z 270.0 fragments further to give an ion at m/z 186.0 (major) and ion at m/z 184.0 (minor) with a neutral loss of –[84] and –[86] respectively further confirming the identity of the compound.
Figure 10:
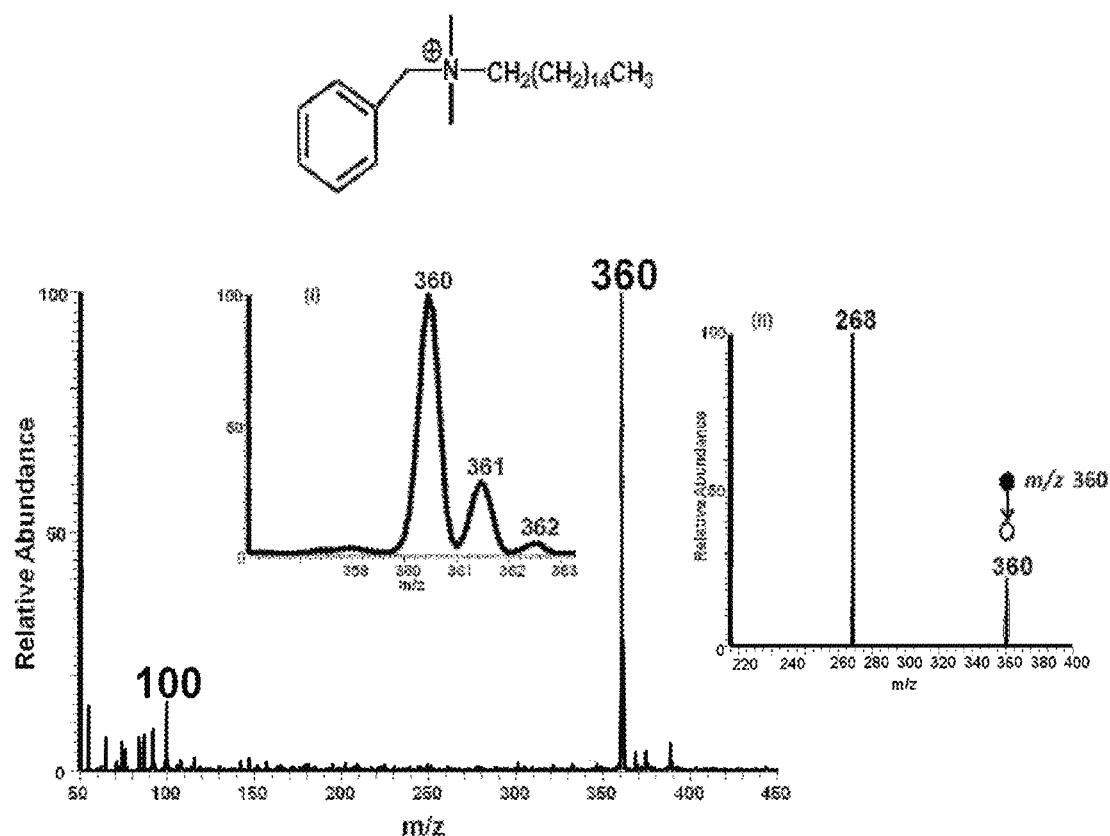
FIG. 10 is a positive paper spray-MS mass spectrum of benylhexadecyldimethylammonium chloride. Insert (i) shows the Isotopic distribution of the analyte ion, (ii) Tandem mass spectrometry (MS/MS) of the benylhexadecyldimethylammonium cation at m/z 360 gives a major fragment ion at m/z 268 with a loss of alkene –[92] that confirms the structure.

The paper spray ambient ionization/Mini 12.0 combination was also used for mixture analysis. To test this capability, a standard mixture of alkyldimethylbenzylammonium chloride (i.e., a salt having n-alkyl substituents $C_{12}$ (major), $C_{14}$ and $C_{16}$) obtained from Sigma Aldrich (St. Louis, Mo.) was dissolved in pump oil. A second mixture consisting of five corrosion inhibitors dissolved in methanol/acetonitrile (1:1, v/v) was prepared in house by mixing equal amounts of tetrabutylammonium bromide, hexadecytrimethylammonium bromide, benzylhexadecyldimethylammonium chloride, tetraoctylammonium bromide and tetradodecylammonium bromide in pump oil. Typical mass spectra obtained for the two different mixtures using the Mini 12.0 are shown in FIGS. 6A-B, when 100 µg/µL was examined on paper using the Mini 12.0 instrument. For the artificial quaternary ammonium salt mixture, the components in the mixture were observed at m/z 242, 284, 354, 360 and 466. For the standard mixture of trialkylarylammonium salts, only two out of the three mixture components (i.e., $C_{12}$ and $C_{14}$) were typically observed in the full scan mode using either the benchtop commercial or the Mini 12.0 instruments (FIG. 6B) when 1 ng/µL of the mixture was spiked onto the paper. This is simply because the amount of m/z 360 ($C_{16}$) benzylhexadecyldimethylammonium chloride salt in the mixture was smaller than that of m/z 332 ($C_{14}$), which was in turn smaller than m/z 304 ($C_{12}$). The m/z 360 ($C_{16}$) component could, however, be identified and confirmed at m/z 360 using the MS/MS experiment as shown in FIG. 3A, insert iii) and FIG. 4B. Structural information was obtained for each member of the two mixtures, examples of which are provided in FIGS. 6C-D using the Mini 12.0 handheld miniature mass spectrometer.

Direct analysis of corrosion inhibitor active components at very low concentrations (<1 ng/µL) in complex oil mixtures has been demonstrated using paper spray ionization using a portable handheld mass spectrometer. The MS/MS experiment provides a powerful means of qualitative analysis. The resolution of the miniature ion trap instrument is adequate for these experiments (unit resolution over the mass range of interest) and the detection limit is only a factor of ca. 10 more than in the commercial bench-top instrument. This detection limit is adequate for the direct detection of corrosion inhibitor concentration levels. Hence the results shown provide evidence that the described techniques can be used for the analysis of corrosion inhibitor concentrations at levels appropriate to manage the treatment of transmission pipelines.

What is claimed is:

1. A method for analyzing a crude oil sample, the method comprising:
    obtaining a crude oil sample comprising a non-naturally occurring substance within the crude oil sample;
    introducing the crude oil sample to a porous paper substrate;
    applying solvent and voltage to the crude oil sample on the substrate to generate ions of the non-naturally occurring substance directly and only from the crude oil sample, wherein the applying step is conducted without an external heat source; and
    analyzing the ions using a mass spectrometer, wherein the method is performed without pre-purification of the crude oil sample.

2. The method according to claim 1, wherein the mass spectrometer is selected from the group consisting of a bench-top mass spectrometer and a miniature mass spectrometer.

3. The method according to claim 1, wherein the non-naturally occurring substance in the crude oil is a corrosion inhibitor.

4. The method according to claim 3, wherein the corrosion inhibitor comprises at least one alkyl ammonium salt.

5. The method according to claim 4, wherein the alkyl ammonium salt is selected from the group consisting of tetradodecylammonium bromide, benzylhexadecyldimethylammonium chloride, and a combination thereof.

6. The method according to claim 1, wherein the mass spectrometer is coupled with a discontinuous atmospheric pressure interface.

7. The method according to claim 1, wherein the solvent comprises a mixture of methanol and acetonitrile.

* * * * *